(12) United States Patent
Hagihara

(10) Patent No.: US 10,432,882 B2
(45) Date of Patent: Oct. 1, 2019

(54) IMAGING DEVICE AND ENDOSCOPE SYSTEM

(71) Applicant: OLYMPUS CORPORATION, Hachioji-shi, Tokyo (JP)

(72) Inventor: Yoshio Hagihara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 62 days.

(21) Appl. No.: 15/876,494

(22) Filed: Jan. 22, 2018

(65) Prior Publication Data

US 2018/0146152 A1    May 24, 2018

Related U.S. Application Data

(63) Continuation of application No. PCT/JP2015/072346, filed on Aug. 6, 2015.

(51) Int. Cl.
*H04N 5/374* (2011.01)
*H04N 5/378* (2011.01)
(Continued)

(52) U.S. Cl.
CPC .............. *H04N 5/374* (2013.01); *A61B 1/045* (2013.01); *A61B 1/051* (2013.01); *H04N 5/2256* (2013.01);
(Continued)

(58) Field of Classification Search
CPC ...... H04N 5/374; H04N 5/361; H04N 5/2256; H04N 5/378; H04N 2005/2255;
(Continued)

(56) References Cited

U.S. PATENT DOCUMENTS

| 6,704,050 B1 * | 3/2004 | Washkurak ............ H04N 5/378 250/208.1 |
| 2004/0027471 A1 | 2/2004 | Koseki et al. |

(Continued)

FOREIGN PATENT DOCUMENTS

| JP | 2003-198944 A | 7/2003 |
| JP | 2003-348464 A | 12/2003 |

(Continued)

OTHER PUBLICATIONS

International Search Reported dated Oct. 20, 2015, issued in Counterpart of International Application No. PCT/JP2015/072346 (3 pages).

*Primary Examiner* — Jared Walker
(74) *Attorney, Agent, or Firm* — Westerman, Hattori, Daniels & Adrian, LLP

(57) ABSTRACT

An imaging device includes a plurality of pixels, a reference current generation circuit, a differential current generation circuit, a reference voltage generation circuit, a conversion circuit, and an output circuit. The differential current generation circuit generates a differential current according to a difference between a pixel current and a reference current. The conversion circuit converts the differential current into an output voltage on the basis of a first reference voltage. A second reference voltage is higher than the tint reference voltage when the output voltage at the time of resetting of the pixels is higher than the output voltage at the time of exposure of the pixels. The second reference voltage is lower than the first reference voltage when the output voltage at the time of resetting of the pixels is lower than the output voltage at the time of exposure of the pixels.

6 Claims, 12 Drawing Sheets

(51) Int. Cl.
    *A61B 1/05*     (2006.01)
    *H04N 5/225*     (2006.01)
    *A61B 1/045*     (2006.01)
    *H04N 5/361*     (2011.01)
    *A61B 1/07*     (2006.01)
    *G02B 23/24*     (2006.01)
    *A61B 1/06*     (2006.01)

(52) U.S. Cl.
    CPC ............ *H04N 5/361* (2013.01); *H04N 5/378* (2013.01); *A61B 1/0669* (2013.01); *A61B 1/07* (2013.01); *G02B 23/2446* (2013.01); *G02B 23/2469* (2013.01); *H04N 2005/2255* (2013.01)

(58) Field of Classification Search
    CPC ........... A61B 1/051; A61B 1/045; A61B 1/07; A61B 1/0669; G02B 23/2469; G02B 23/2446
    USPC .......................................................... 348/76
    See application file for complete search history.

(56) References Cited

U.S. PATENT DOCUMENTS

| | | | |
|---|---|---|---|
| 2011/0062310 A1* | 3/2011 | Kudo ................... | H04N 5/2176 250/208.1 |
| 2013/0093868 A1* | 4/2013 | Hagihara ............. | H04N 5/3745 348/76 |
| 2013/0234004 A1* | 9/2013 | Hagihara ............... | H04N 5/378 250/208.1 |

FOREIGN PATENT DOCUMENTS

| | | |
|---|---|---|
| JP | 2013-90036 A | 5/2013 |
| WO | 2014/175005 A1 | 10/2014 |

* cited by examiner

IMAGING DEVICE AND ENDOSCOPE SYSTEM

BACKGROUND OF THE INVENTION

Field of the Invention

The present invention relates to an imaging device and an endoscope system.

This application is a continuation application based on International Patent Application No. PCT/JP2015/072346, filed on Aug. 6, 2015, the content of which is incorporated herein by reference.

Description of Related Art

Various types of imaging devices such as a metal oxide semiconductor (MOS) type and a charge coupled device (CCD) type have been proposed and put to practical use. Examples of the MOS type imaging device include a (C)MOS type imaging device including pixels having an active pixel sensor (APS) configuration. The pixel having the APS configuration amplifies a pixel signal according to signal charge generated by a photoelectric conversion unit and outputs the amplified pixel signal.

For example, a (C)MOS type imaging device is disclosed in Japanese Unexamined Patent Application, First Publication No. 2013-90036. A configuration of the (C)MOS type imaging device of the related art will be described. FIG. 9 shows a configuration of an imaging device 1001 of the related art. As shown in FIG. 9, the imaging device 1001 includes an imaging unit 1002, a vertical selection unit 1004, a switch unit 1005, a horizontal selection unit 1006, and an output unit 1007.

The imaging unit 1002 includes a plurality of pixels 1003 arranged in a matrix form. The plurality of pixels 1003 constitute an an of m rows and n columns. m and n are integers greater than or equal to 2. Each of the plurality of pixels 1003 includes a photoelectric conversion unit PD, a transfer transistor Tx, a charge accumulation unit FD, a reset transistor Rst, an amplification transistor Drv, and a selection transistor Sel.

For example, the photoelectric conversion unit PD is a photodiode. The transfer transistor Tx is controlled by a transfer pulse ϕTx that is output from the vertical selection unit 1004. The reset transistor Rst is controlled by a reset pulse ϕRst that is output from the vertical selection unit 1004. The selection transistor Sel is controlled by a selection pulse ϕSel that is output from the vertical selection unit 1004.

The photoelectric conversion unit PD generates signal charge according to an amount of incident light. The transfer transistor Tx transfers the signal charge generated by the photoelectric conversion unit PD to the charge accumulation unit FD. For example, the charge accumulation unit FD is a floating diffusion. The charge accumulation unit FD accumulates the signal charge transferred by the transfer transistor Tx. The reset transistor Rst resets the charge accumulatior FD to a predetermined voltage. An amplification transistor Drv generates a pixel signal by amplifying a signal according to the voltage of the charge accumulation unit FD. The selection transistor Sel outputs the pixel signal to a vertical signal line 1030. A vertical signal line 1030 is arranged in each column in the array of the plurality of pixels 1003. A reset level and a signal level are output from the pixel 1003 as pixel signals.

The vertical selection unit 1004 selects the plurality of pixels 1003 arranged in a row direction in the array of the plurality of pixels 1003. The vertical selection unit 1004 controls an operation of the selected pixels 1003. The vertical selection unit 1004 outputs a control signal for controlling the plurality of pixels 1003 to each row in the array of the plurality of pixels 1003. The control signal output from the vertical selection unit 1004 includes the transfer pulse ϕTx, the reset pulse ϕRst, and the selection pulse ϕSel.

The switch unit 1005 includes a switch transistor SW arranged in each column in the array of the plurality of pixels 1003. The switch transistor SW is connected to the vertical signal line 1030 and a horizontal signal line 1031. The horizontal signal line 1031 is arranged in the row direction in the array of the plurality of pixels 1003. The switch transistor SW outputs the pixel signal, which has been output to the vertical signal line 1030, to the horizontal signal line 1031. The switch transistor SW in the i-th column is controlled by a selection pulse HSR[i] that is output from the horizontal selection unit 1006. i is an integer greater than or equal to 1 and smaller than or equal to n.

The horizontal signal line 1031 is connected to the output unit 1007. The horizontal selection unit 1006 sequentially selects the switch transistors SW using the selection pulse HSR[1] to the selection pulse HSR[n], and transfers the pixel signal to the output unit 1007. This pixel signal is input to the output unit 1007 as a current. The output unit 1007 converts the pixel signal into an output voltage and outputs the output voltage as an output signal Aout to a subsequent-stage circuit 1200 (FIG. 11).

FIG. 10 shows a configuration of the output unit 1007. As shown in FIG. 10, the output unit 1007 includes a current mirror unit CM1 and a conversion unit I/V1.

The current mirror unit CM1 includes a transistor N1 and a transistor N2. The transistors N1 and N2 are NMOS transistors. A drain terminal of the transistor N1 is connected to the horizontal signal line 1031. A source terminal of the transistor N1 is connected to a ground. A gate terminal of the transistor N1 is connected to the drain terminal of the transistor N1. A drain terminal of the transistor N2 is connected to the conversion unit I/V1. A source terminal of the transistor N2 is connected to the ground. A gate terminal of the transistor N2 is connected to the gate terminal of the transistor N1.

The conversion unit I/V1 is a current-voltage conversion amplifier for converting a current into an output voltage and outputting the output voltage. The conversion unit I/V1 includes a resistor R1 and an operational amplifier OP1. A first terminal of the resistor R1 is connected to the drain terminal of the transistor N2 and an inverting input terminal of the operational amplifier OP1. A second terminal of the resistor R1 is connected to an output terminal of the operational amplifier OP1. A non-inverting input terminal of the operational amplifier OP1 is connected to a power supply that outputs a reference voltage.

In FIG. 10, the amplification transistors Drv and the selection transistors Sel in some of the pixels 1003 of the imaging unit 1002 are shown. Further, in FIG. 10, some of the switch transistors SW of the switch unit 1005 are shown.

A current based on the pixel signal output from the pixel 1003 is input to the current mirror unit CM1. The current mirror unit CM1 returns the current using the transistor N1 and the transistor N2. That is, when a mirror ratio is 1:1, the current mirror unit CM1 generates the same current as the current output from the pixel 1003. The current generated by the current mirror unit CM1 is output to the conversion unit I/V1. The conversion unit I/V1 converts the current to the output voltage and outputs the output voltage as the output signal Aout to the subsequent-stage circuit 1200.

Equation (1) shows a voltage value $V_{OUT}$ of the output signal Aout of the conversion unit I/V1.

$$V_{OUT}=V_{REF}+R_1 \times I_{PIX} \qquad (1)$$

In Equation (1), the voltage value $V_{REF}$ is a value of the reference voltage. The resistance value $R_1$ is a value of the resistor $R_1$. The current value $I_{PIX}$ is a value of the current generated by the current mirror unit CM1. As shown in Equation (1), the conversion unit I/V1 converts the current ($I_{PIX}$) into the output voltage ($V_{OUT}$) whose reference is the reference voltage ($V_{REF}$).

The subsequent-stage circuit 1200 obtains a signal component which is a difference between the reset level and the signal level by performing subtraction (CDS process). FIG. 11 shows a configuration of the subsequent-stage circuit 1200. As shown in FIG. 11, the subsequent-stage circuit 1200 includes an AD conversion circuit 1201, a line memory 1202, and a subtractor 1203.

The output signal Aout from the output unit 1007 is input to the AD conversion circuit 1201. The AD conversion circuit 1201 converts the output signal Aout into a digital value. The line memory 1202 holds the digital value of the output voltage at the reset level. The subtractor 1203 subtracts the digital value of the output voltage at the reset level held in the line memory 1202 from the digital value of the output voltage at the signal level output from the AD conversion circuit 1201. The subtractor 1203 outputs a digital value Asub of the sisal component.

An operation of the (C)MOS type imaging device of the related art will be described. FIG. 12 shows an operation of the imaging device 1001. Hereinafter, an operation of reading the pixel signal in the imaging device 1001 will be described.

FIG. 12, waveforms of the selection pulse φSel, the reset pulse φRst, the transfer pulse φTx, the selection pulse HSR[1] to the selection pulse HSR[n], and the output signal bout are shown. In FIG. 12, a horizontal direction indicates time and a vertical direction indicates a voltage.

Before the operation of reading the pixel signal is started, the selection pulse φSel, the reset pulse φRst, the transfer pulse φTx, and the selection pulse HSR[1] to the selection pulse HSR[n] are L (Low) state. Before the operation of reading the pixel signal is started, the output signal Aout is at a ground level (GND).

The selection pulse φSel output from the vertical selection it 1004 to the pixel 1003 in a predetermined row changes from an L state to a H (High) state, and accordingly, the selection transistor Sel is turned on (becomes a conducting state). Accordingly, the pixel 1003 in a predetermined row is selected.

(Reading of Reset Level)

The reset pulse φRst output from a vertical selection unit 4 to the pixel 1003 in the predetermined row changes from the L state to the H state, and accordingly, the reset transistor Rst is turned on. Accordingly, the charge accumulation unit FD is reset and the pixel signal at the reset level is output to the vertical signal line 1030. Thereafter, the reset pulse φRst changes from the H state to the L state, and accordingly, the reset transistor Rst is turned off.

Thereafter, the selection pulse HSR[1] output from the horizontal selection unit 1006 to the switch transistor SW in the first column changes from the L state to the H state, and accordingly, the switch transistor SW is turned on. Accordingly, the pixel signal at the reset level of the pixel 1003 in the first column in a predetermined row is output from the vertical signal line 1030 to the horizontal signal line 1031. In this case, reading of the reset level is started. The pixel signal at the reset level output to the horizontal signal line 1031 is input to the output unit 1007. The output unit 1007 converts the pixel signal at the reset level input as a current into an output voltage, and outputs the output voltage as the output signal Aout to the subsequent-stage circuit 200. Then, the selection pulse HSR[1] changes from the H state to the L state, and accordingly, the switch transistor SW is turned off.

Similarly, the selection pulse HSR[2] to the selection pulse HSR[n] sequentially become the H state, and accordingly, the pixel signal at the reset level is transferred from the pixel 1003 of each column in the predetermined row to the output unit 1007. The output unit 1007 converts the sequentially input pixel signals at the reset level into the output voltages and outputs the output voltages as the output signals Aout to the subsequent-stage circuit 1200. The selection pulse HSR[n] becomes the L state, and accordingly, the rending of the reset level ends.

In each period in which the selection pulse HSR[1] to the selection pulse HSR[n] are in the H state, the AD conversion circuit 1201 of the subsequent-stage circuit 1200 converts the output voltage at the reset level into a digital value. The line memory 1202 holds the digital value of the output voltage at the reset level.

(Reading of Signal Level)

Thereafter, the transfer pulse φTx output from the vertical selection unit 1004 to the pixel 1003 in the predetermined row changes from the L state to the H state, and accordingly, the transfer transistor Tx is turned on. Accordingly, the signal charge of the photoelectric conversion unit PD is transferred to the charge accumulation unit FD, and the pixel signal at the signal level is output to the vertical signal line 1030. Thereafter, the transfer pulse φTx changes from the H state to the L state, and accordingly, the transfer transistor Tx is turned off.

Thereafter, the selection pulse HSR[1] output from the horizontal selection unit 1006 to the switch transistor SW in the first column changes from the L state to the H state, and accordingly, the switch transistor SW is turned on. Accordingly, the pixel signal at the signal level of the pixel 1003 of the first column in the predetermined row is output from the vertical signal line 1030 to the horizontal signal line 1031. In this case, reading of the signal level is started. The pixel signal at the signal level output to the horizontal signal line 1031 is input to the output unit 1007. The output unit 1007 converts the pixel signal at the signal level input as a current into an output voltage, and outputs the output voltage as the output signal Aout to the subsequent-stage circuit 1200. Thereafter, the selection pulse HSR[1] changes from the H state to the L state, and accordingly, the switch transistor SW is turned off.

Similarly, the selection pulse HSR[2] to the selection pulse HSR[n] sequentially become the H state, and accordingly, the pixel signal at the signal level is transferred from the pixel 1003 of each column in the predetermined row to the output unit 1007. The output unit 1007 converts the sequentially input pixel signals at the signal level to the output voltages and outputs the output voltage as the output signals Aout to the subsequent stage circuit 1200. The selection pulse HSR[n] becomes the L state, and accordingly, the reading of the signal level ends.

In each period in which the selection pulse HSR[1] to the selection pulse HSR[n] are in the H state, the AD conversion circuit 1201 of the subsequent-stage circuit 1200 converts the output voltage at the signal level to a digital value. The subtractor 1203 subtracts the digital value of the output voltage at the reset level held in the line memory 1202 from the digital value of the output voltage at the signal level.

By performing the above operation for each row, pixel signals are read from the pixels 1003 of all the rows.

SUMMARY OF THE INVENTION

According to a first aspect of the present invention, an imaging device includes a plurality of pixels, a reference current generation circuit, a differential current generation circuit, a reference voltage generation circuit, a conversion circuit, and an output circuit. The plurality of pixels output a pixel current according to incident light. The reference current generation circuit generates a reference current. The differential current generation circuit receives the pixel current and the reference current and generates a differential current according to a difference between the pixel current and the reference current. The reference voltage generation circuit generates a first reference voltage and a second reference voltage. The conversion circuit receives the differential current and the first reference voltage, and converts the differential current into an output voltage on the basis of the first reference voltage. The output circuit receives the output voltage and the second reference voltage, and outputs the output voltage and the second reference voltage. The second reference voltage is higher than the first reference voltage when the output voltage at the time of resetting of the plurality of pixels is higher than the output voltage at the time of exposure of the plurality of pixels. The second reference voltage is lower than the first reference voltage when the output voltage at the time of resetting of the plurality of pixels is lower than the output voltage at the time of exposure of the plurality of pixels.

According to a second aspect of the present invention, in the first aspect, the output circuit may alternately output the output voltage and the second reference voltage.

According to a third aspect of the present invention, in the first aspect, each of the plurality of pixels may include a photoelectric conversion unit, a charge transfer unit, a charge accumulation unit, and a signal generation unit. The photoelectric conversion unit may generate signal charge according to the incident light. The charge transfer unit may transfer the signal charge generated by the photoelectric conversion unit. The charge accumulation unit may accumulate the signal charge transferred by the charge transfer unit. The signal generation unit may generate the pixel current according to the voltage of the charge accumulation unit. The signal generation unit may be a first MOS transistor. The first MOS transistor may have a first drain terminal and a first source terminal, and the pixel current may flow between the first drain terminal and the first source terminal. The reference current generation circuit may include a second MOS transistor. The second MOS transistor may have a gate terminal, a second drain terminal, and a second source terminal, and the reference current may flow between the second drain terminal and the second source terminal. The gate terminal and the second drain terminal may be electrically connected to each other.

According to a fourth aspect of the present invention, in the first aspect, each of the plurality of pixels may include a photoelectric conversion unit, a charge transfer unit, a charge accumulation unit, and a signal generation unit. The photoelectric conversion unit may generate signal charge according to the incident light. The charge transfer unit may transfer the signal charge generated by the photoelectric conversion unit. The charge accumulation unit may accumulate the signal charge transferred by the charge transfer unit. The signal generation unit may generate the pixel current according to the voltage of the charge accumulation unit. The signal generation unit may be a first MOS transistor. The first MOS transistor may have a first drain terminal and a first source terminal, and the pixel current may flow between the first drain terminal and the first source terminal. The reference current generation circuit may include a second MOS transistor, a switch, and a capacitive element. The second MOS transistor may have a gate terminal, a second drain terminal, and a second source terminal, and the reference current may flow between the second drain terminal and the second source terminal. The switch may have a first terminal connected to the gate terminal and a second terminal connected to the second drain terminal. The capacitive element may be connected to the gate terminal.

According to a fifth aspect of the present invention, in the first aspect, each of the plurality of pixels may include a photoelectric conversion unit, a charge transfer unit, a first charge accumulation unit, and a signal generation unit. The photoelectric conversion unit may generate first signal charge according to the incident light. The charge transfer unit may transfer the first signal charge generated by the photoelectric conversion unit. The first charge accumulation unit may accumulate the first signal charge transferred by the charge transfer unit. The signal generation unit may generate the pixel current according to the voltage of the first charge accumulation unit. The signal generation unit may be a first MOS transistor. The first MOS transistor may have a first drain terminal and a first source terminal, and the pixel current may flow between the first drain terminal and the first source terminal. The reference current generation circuit may include a plurality of second charge accumulation units that accumulate second signal charge, and a plurality of second MOS transistors. Each of the plurality of second MOS transistors may have a gate terminal, a second drain terminal, and a second source terminal, and the reference current may flow between the second drain terminal and the second source terminal. Each of the plurality of second charge accumulation units may be connected to the gate terminal of each of the plurality of second MOS transistors. The gate terminals of the plurality of second MOS transistors may be connected to each other.

According to a sixth aspect of the present invention, an endoscope system includes the imaging device according to any one of the first to fifth aspects.

DETAILED DESCRIPTION OF THE INVENTION

Embodiments of the present invention will be described with reference the drawings.

First Embodiment

Figure 1:
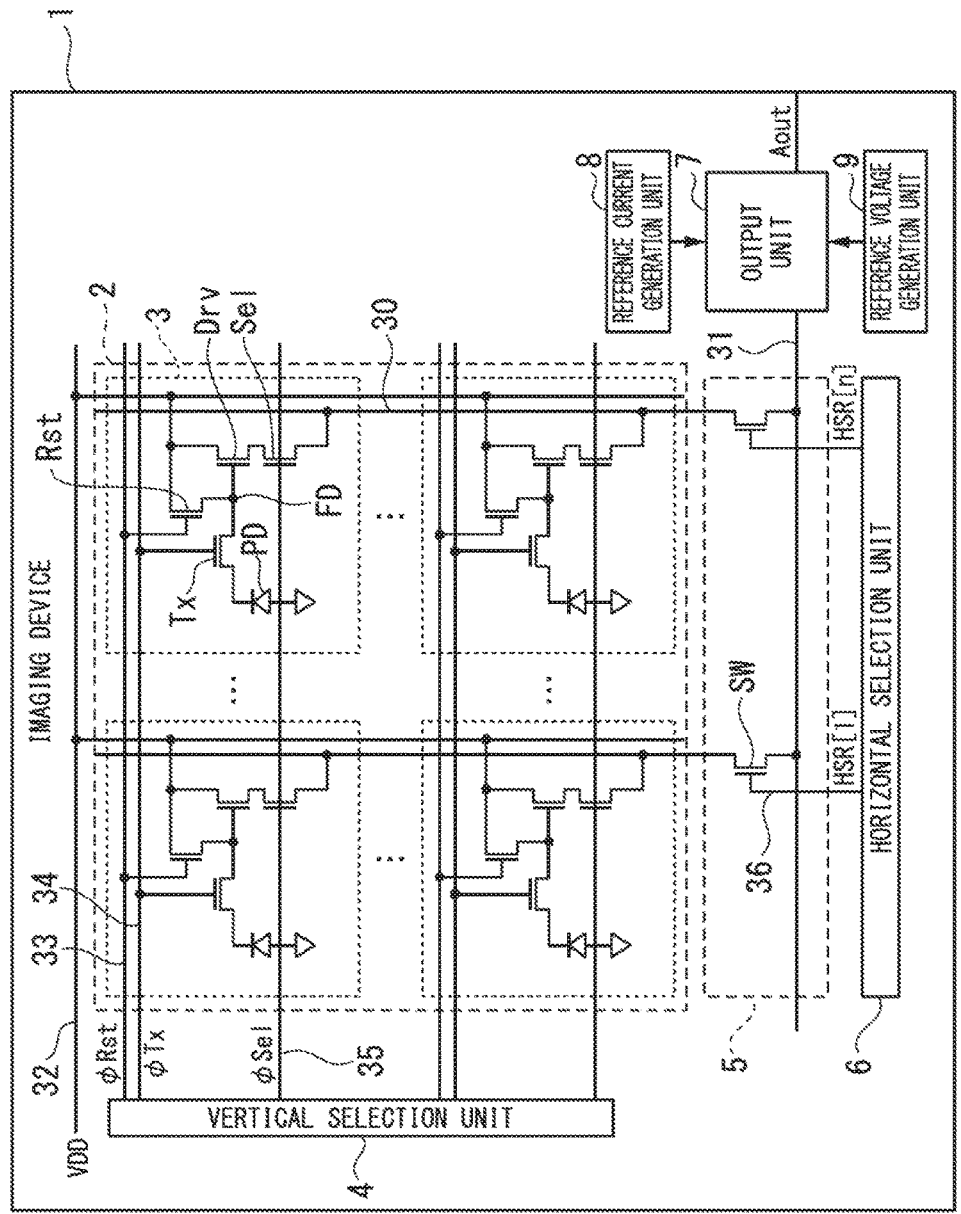
FIG. 1 is a block diagram showing a configuration of an imaging device according to a fir t embodiment of the present invention.

FIG. 1 shows a configuration of an imaging device 1 according to a first embodiment of the present invention. As shown in FIG. 1, the imaging device 1 includes an imaging unit 2, a vertical selection unit 4, a switch unit 5, a horizontal selection unit 6, an output unit 7, a reference current generation unit 8 (reference current generation circuit), and a reference voltage generation unit 9 (reference voltage generation circuit). For example, the imaging unit 2, the vertical selection unit 4, the switch unit 5, the horizontal selection unit 6, the output unit 7, the reference current generation unit 8, and the reference voltage generation unit 9 are arranged on the same substrate or chip.

The imaging unit 2 includes a plurality of pixels 3 arranged in a matrix form. The plurality of pixels 3 constitute an array of m rows and n columns. m and n are integers greater than or equal to 2. The number of rows and the number of columns need not be the same. Each of the plurality of pixels 3 includes a photoelectric conversion unit PD, a transfer transistor Tx (charge transfer unit), a charge accumulation unit FD, a reset transistor Rst a amplification transistor Drv (signal generation unit), and a selection transistor Sel. For example, each of the transfer transistor Tx, the reset transistor Rst, the amplification transistor Drv, and the selection transistor Sel is an NMOS transistor. Each of the transfer transistor Tx, the reset transistor Rst, the amplification transistor Drv, and the selection transistor Sel has a gate terminal, a source terminal, and a drain terminal.

For example, the photoelectric conversion unit PD is a photodiode. A first terminal of the photoelectric conversion unit PD is connected to the ground. A second terminal of the photoelectric conversion unit PD is connected to the transfer transistor Tx.

The source terminal of the transfer transistor Tx is connected to the second terminal of the photoelectric conversion unit PD. The drain terminal of the transfer transistor Tx is connected to the charge accumulation unit FD. The gate terminal of the transfer transistor Tx is connected to a control signal line 34. The control signal line 34 extends in a row direction in the array of the plurality of pixels 3 from the vertical selection unit 4. The control signal line 34 transmits a transfer pulse ϕTx.

The drain terminal of the reset transistor Rst is connected to a power supply line 32. The power supply line 32 is connected to a power supply that outputs a power supply voltage VDD. The source terminal of the reset transistor Rst is connected to the charge accumulation unit FD. The gate terminal of the reset transistor Rst is connected to a control signal line 33. The control signal line 33 extends in the row direction in the array of the plurality of pixels 3 from the vertical selection unit 4. The control signal line 33 transmits a reset pulse ϕRst.

The drain terminal of the amplification transistor Drv is connected to the power supply line 32. The source terminal of the amplification transistor Drv is connected to the selection transistor Sel. The gate terminal of the amplification transistor Drv is connected to the charge accumulation unit FD.

The drain terminal of the selection transistor Sel is connected to the source terminal of the amplification transistor Drv. The source terminal of the selection transistor Sel is connected to a vertical signal line 30. The gate terminal of the selection transistor Sel is connected to a control signal line 35. The control signal line 35 extends in the row direction in the array of the plurality of pixels 3 from the vertical selection unit 4. The control signal line 35 transmits a selection pulse ϕSel.

The transfer transistor Tx is controlled by the transfer pulse ϕTx output from the vertical selection unit 4. The reset transistor Rst is controlled by the reset pulse ϕRst output from the vertical selection unit 4. The selection transistor Sel is controlled by the selection pulse ϕSel output from the vertical selection unit 4.

The photoelectric conversion unit PD generates signal charge according to an amount of incident light. The transfer transistor Tx transfers the signal charge generated by the photoelectric conversion unit PD to the charge accumulation unit FD. For example, the charge accumulation unit FD is a floating diffusion. The charge accumulation unit FD accumulates the signal charge transferred by the transfer transistor Tx. The reset transistor Rst resets the charge accumulation unit FD to a predetermined voltage. The amplification transistor Drv generates a pixel signal by amplifying a signal according the voltage of the charge accumulation unit FD. The selection transistor Sel outputs the pixel signal to the vertical signal line 30. The vertical signal line 30 is arranged in each column in the array of the plurality of pixels 3. A reset level and a signal level are output from the pixel 3 as pixel signals.

With the above configuration, the plurality of pixels 3 output pixel signals (pixel currents) according to incident light. The pixel signal has a current value according to incident light.

The vertical selection unit 4 selects a plurality of pixels 3 arranged in the row direction in the array of the plurality of pixels 3. The vertical selection unit 4 controls an operation of the selected pixels 3. The vertical selection unit 4 outputs a control signal for controlling the plurality of pixels 3 to each row in the array of the plurality of pixels 3. The control signal output from the vertical selection unit 4 includes the transfer pulse ϕTx, the reset pulse ϕRst, and the selection pulse ϕSel.

The switch unit 5 has switch transistors SW arranged in the respective columns in the array of the plurality of pixels 3. The switch transistor SW is connected to the vertical signal line 30 and the horizontal signal line 31. The horizontal signal line 31 is arranged in the row direction in the array of the plurality of pixels 3. For example, the switch transistor SW is an NMOS transistor. The switch transistor SW has a gate terminal, a source terminal, and a drain terminal. The drain terminal of the switch transistor SW is connected to the vertical signal line 30. The source terminal of the switch transistor SW is connected to the horizontal signal line 31. The gate terminal of the switch transistor SW is connected to the control signal line 36. The control signal line 36 extends in the column direction in the array of the plurality of pixels 3 from the horizontal selection unit 6. The control signal line 36 transmits a selection pulse HSR[1] to a selection pulse HSR[n]. The switch transistor SW in the i-th column is controlled by the selection pulse HSR[i] output from the horizontal selection unit 6. i is an integer greater than or equal to 1 and smaller than or equal to n. The switch transistor SW outputs the pixel signal, which has been output to the vertical signal line 30, to the horizontal signal line 31.

Figure 3:
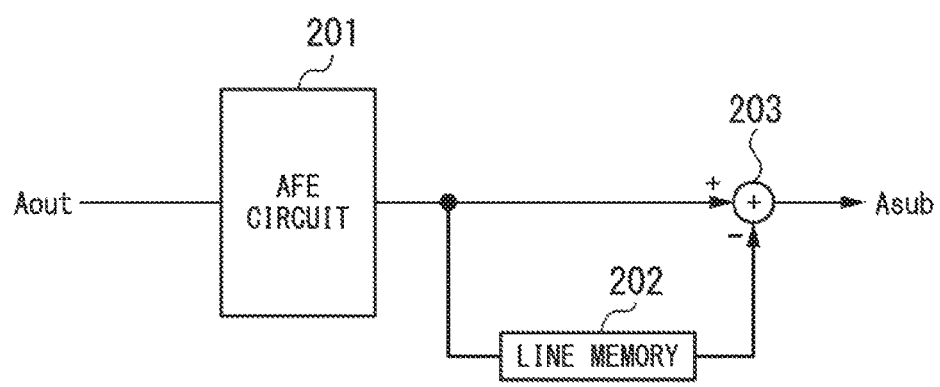
FIG. 3 is a block diagram showing a configuration of a subsequent-stage circuit according to the first embodiment of the present invention.

The horizontal signal line 31 is connected to the output unit 7. The horizontal selection unit 6 sequentially selects the switch transistors SW using the selection pulse HSR[1] to the selection pulse HSR[n] and transfers the pixel signal to the output unit 7. The pixel signal is input to the output unit 7 as a current. The output unit 7 converts the pixel signal into an output voltage and outputs the output voltage as an output signal Aout to a subsequent-stage circuit 200 (FIG. 3). A reference current generation unit 8 generates a reference current and outputs the reference current to the output unit 7. The reference voltage generation unit 9 generates a reference voltage and outputs the reference voltage to the output unit 7.

Figure 2:
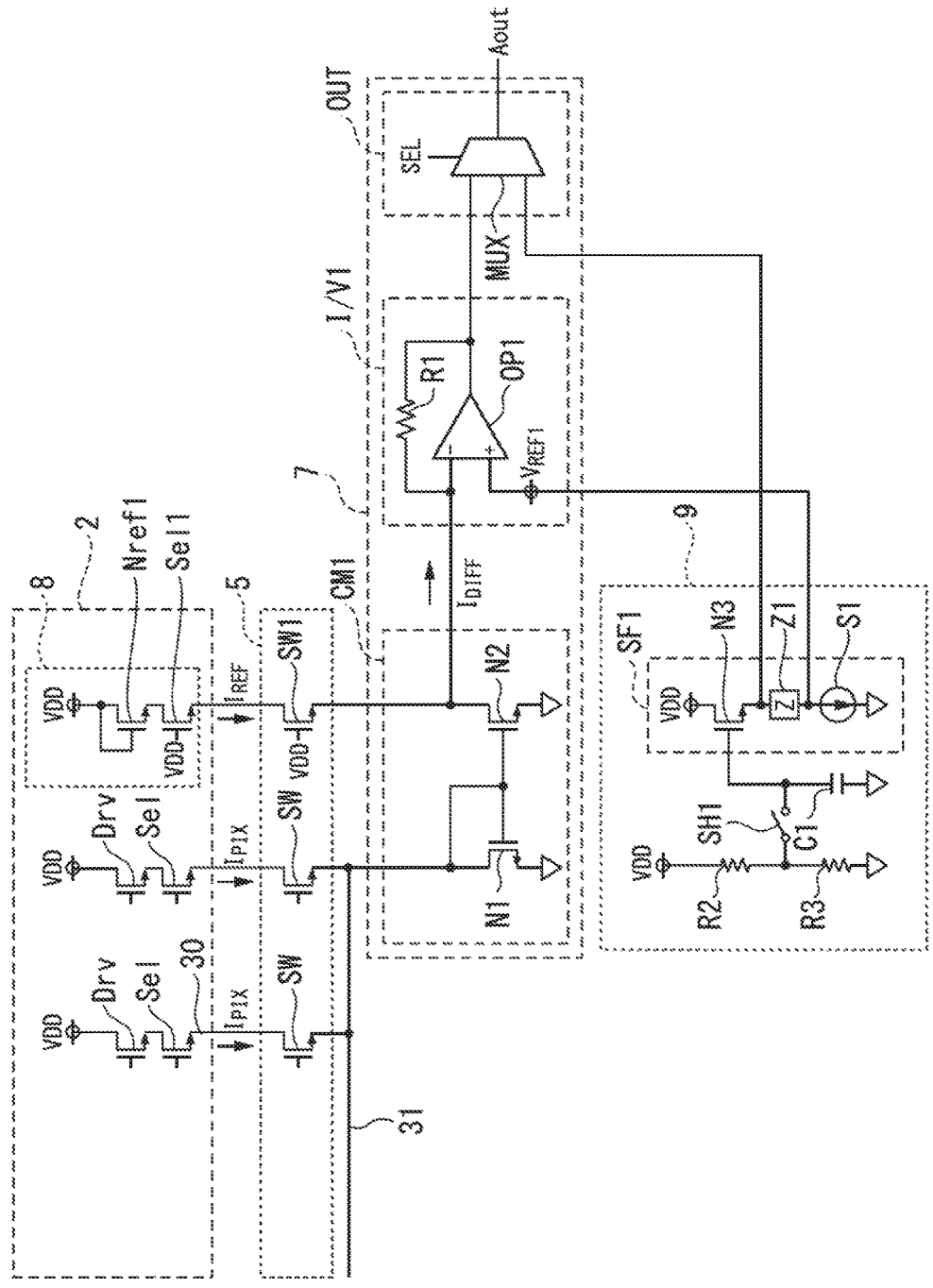
FIG. 2 is a circuit diagram showing a configuration of an output unit, a reference current generation unit, and a reference voltage generation unit in the imaging device according to the first embodiment of the present invention.

FIG. 2 shows a configuration of the output unit 7, the reference current generation unit 8, and the reference voltage generation unit 9. As shown in FIG. 2, the reference current generation unit 8 includes a transistor Nref1 and a selection transistor Sel1. For example, the transistor Nref1 and the selection transistor Sel1 are NMOS transistors. The transistor Nref1 and the selection transistor Sel1 have a gate terminal, a source terminal, and a drain terminal.

The drain terminal of the transistor Nref1 is connected to a power supply that outputs a power supply voltage VDD. The source terminal of the transistor Nref1 is connected to the selection transistor Sel1. The gate terminal of the transistor Nref1 is connected to the drain terminal of the transistor Nref1. The transistor Nref1 outputs the reference current from the source terminal. For example, the current value of the reference current is the same as a current value of the pixel signal at the time of darkness when the amount of incident light is substantially zero.

The drain terminal of the selection transistor Sel1 is connected to the source terminal of the transistor Nref1. The source terminal of the selection transistor Sel1 is connected to the switch unit 5. The gate terminal of the selection transistor Sel1 is connected to a power supply that outputs the power supply voltage VDD. A reference current flows between the drain terminal of the selection transistor Sel1 and the source terminal of the selection transistor Sel1. The selection transistor Sel1 outputs, from the source terminal, the reference current output from the transistor Nref1.

A configuration of the reference current generation unit 8 is not limited to the above configuration. The reference current generation unit 8 may be configured similarly to the pixel 3. For example, the transistor Nref1 may be configured similarly to the amplification transistor Drv. For example, the selection transistor Sel1 may be configured similarly to the selection transistor Sel. In FIG. 2, the transistor Nref1 and the selection transistor Sel1 are part of the imaging unit 2. However, the transistor Nref1 and the selection transistor Sel1 may be configured independently of the imaging unit 2. The transistor Nref1 and the selection transistor Sel1 may be PMOS transistors.

FIG. 2, the amplification transistors Drv and the selection transistors Sel in some of the pixels 3 of the imaging unit 2 are shown. Further, in FIG. 2, some of the switch transistors SW of the switch unit 5 are shown.

As described above, each of the plurality of pixels 3 includes the photoelectric conversion unit PD, the transfer transistor Tx (charge transfer unit), the charge accumulation unit FD, and the signal generation unit. The photoelectric conversion unit PD generates signal charge according to the incident light. The transfer transistor Tx transfers the signal charge generated by the photoelectric conversion unit PD. The charge accumulation unit FD accumulates the signal charge transferred by the transfer transistor Tx. The signal generation unit generates a pixel current according to the voltage of the charge accumulation unit FD. The signal generation unit is the amplification transistor Drv (first MOS transistor). The amplification transistor Drv has the drain terminal (a first drain terminal) and the source terminal (a first source terminal). A pixel current flows between the drain terminal of the amplification transistor Drv and the source terminal of the amplification transistor Drv.

As described above, the reference current generation unit 8 (reference current generation circuit) includes the transistor Nref1 (second MOS transistor). The transistor Nref1 has the gate terminal, the drain terminal (a second drain terminal), and the source terminal (a second source terminal). The reference current flows between the drain terminal of the transistor Nref1 and the source terminal of the transistor Nref1. The gate terminal of the transistor Nref1 and the drain terminal of the transistor Nref1 are electrically connected.

The switch unit 5 includes a switch transistor SW1 in addition to the plurality of switch transistors SW. For example, the switch transistor SW1 is an NMOS transistor. The switch transistor SW1 has a gate terminal, a source terminal, and a drain terminal. The drain terminal of the switch transistor SW1 is connected to the source terminal of the selection transistor Sel1. The source terminal of the switch transistor SW1 is connected to the output unit 7. The gate terminal of the switch transistor SW1 is connected to the power supply that outputs the power supply voltage VDD. In FIG. 1, the switch transistor SW1 is omitted.

As shown in FIG. 2, the output unit 7 includes a current mirror unit CM1 (differential current generation circuit), a conversion unit I/V1, and an output circuit OUT.

The current mirror unit CM1 includes a transistor N1 and a transistor N2. The transistors N1 and N2 are NMOS transistors. Each of the transistor N1 and the transistor N2 has a gate terminal, a source terminal, and a drain terminal. The drain terminal of the transistor N1 is connected to the horizontal signal line 31. The source terminal of the transistor N1 is connected to a ground. The gate terminal of the transistor N1 is connected to the drain terminal of the transistor N1. The drain terminal of the transistor N2 is connected to the source terminal of the switch transistor SW1 and the conversion unit I/V1. The source terminal of the transistor N2 is connected to the ground. The gate terminal of the transistor N2 and the gate terminal of the transistor N1 are electrically connected to each other.

The conversion unit I/V1 is a current-voltage conversion amplifier for converting a current into an output voltage and outputting the output voltage. The conversion unit I/V1 includes a resistor R1 and an operational amplifier OP1. The resistor R1 has a first terminal and a second terminal. The operational amplifier OP1 has a non-inverting input terminal, an inverting input terminal, and an output terminal. The first terminal of the resistor R1 is connected to the drain terminal of the transistor N2 and the inverting input terminal of the operational amplifier OP1. The second terminal of the resistor R1 is connected to the output terminal of the operational amplifier OP1. The non-inverting input terminal of the operational amplifier OP1 is connected to the reference voltage generation unit 9. The first reference voltage generated by the reference voltage generation unit 9 is input to the non-inverting input terminal of the operational amplifier OP1.

The pixel current based on the pixel signal output from the pixel 3 and the reference current generated by the reference current generation unit 8 are input to the current mirror unit CM1. The pixel current is input to the transistor N1. The pixel current flows between the drain terminal of the transistor N1 and the source terminal of the transistor N1. In the current mirror unit CM1, the current is returned by the transistor N1 and the transistor N2. That is, when a mirror ratio is 1:1, the current minor unit CM1 generates the same current as the pixel current. This current flows between the drain terminal of the transistor N2 and the source terminal of the transistor N2. A difference between the reference current from the reference current generation unit 8 and the current flowing through the transistor N2 is output from the current mirror unit CM1. Accordingly, the current mirror unit CM1 generates a differential current according to the difference between the pixel current and the reference current. The current mirror unit CM1 outputs the generated differential current to the conversion unit I/V1.

The configuration of the current mirror unit CM1 is not limited to the above configuration. For example, the current mirror unit CM1 may amplify the current output from the pixel 3 at a predetermined ratio and return the current.

The differential current generated by the current mirror unit CM1 and the first reference voltage generated by the reference voltage generation unit 9 are input to the conversion unit I/V1. The differential current is input to the inverting input terminal of the operational amplifier OP1. The first reference voltage is input to the non-inverting input terminal of the operational amplifier OP1. The conversion unit I/V1 converts the differential current into an output voltage on the basis of the first reference voltage. The conversion unit I/V1 outputs the generated output voltage to the output circuit OUT.

The output circuit OUT includes a selection circuit MUX. The selection circuit MUX is controlled by a selection signal SEL. The output voltage generated by the conversion unit I/V1 and the second reference voltage generated by the reference voltage generation unit 9 are input to the output circuit OUT, that is, the selection circuit MUX. The output circuit OUT, that is, the selection circuit MUX alternately outputs the output voltage and the second reference voltage as the output signal Aout. That is, the output circuit OUT, that is, the selection circuit MUX outputs the second reference voltage in a first period and outputs the output voltage in the second period. A period during which the pixel signal of one column in the array of the plurality of pixels 3 is output includes the first period and the second period. The second period is after the first period. The output signal Aout is output to the subsequent-stage circuit 200.

The output circuit OUT may simultaneously output the output voltage and the second reference voltage. For example, the output circuit OUT may have an electrode or terminal for outputting the output voltage, and an electrode or terminal for outputting the second reference voltage. Therefore, the output circuit OUT need not include the selection circuit MUX.

The reference voltage generation unit 9 includes a resistor R2, a resistor R3, a switch SH1, a capacitive element C1, and a source follower circuit SF1.

Each of the resistors R2 and R3 has a first terminal and a second terminal. The first terminal of the resistor R2 is connected to the power supply that outputs the power supply voltage VDD. The first terminal of the resistor R3 is connected to the second terminal of the resistor R2. The second terminal of the resistor R3 is connected to the ground.

Each of the switch SH1 and the capacitive element C1 has a first terminal and a second terminal. The first terminal of the switch SH1 is connected to the second terminal of the resistor R2 and the first terminal of the resistor R3. The first terminal of the capacitive element C1 is connected to the second terminal of the switch SH1. The second terminal of the capacitive element C1 is connected to the ground.

The switch SH1 is an element that can switch between ON and OFF. For example, the switch SH1 is a transistor. When the switch SH1 is ON, the first terminal of the capacitive element C1 is electrically connected to the second terminal of the resistor R2 and the first terminal of the resistor R3. When the switch SH1 is OFF, the first terminal of the capacitive element C1 is electrically insulated from the second terminal of the resistor R2 and the first terminal of the resistor R3.

The switch SH1 and the capacitive element C1 constitute a sample and hold circuit. The switch SH1 samples a voltage according to the voltage value of the power supply voltage VDD and the resistance values of the resistor R2 and the resistor R3. The capacitive element C1 holds the voltage sampled by the switch SH1. That is, the capacitive element C1 is a sampling capacitor. By sampling the voltage according to the power supply voltage VDD, the influence of noise superimposed on the power supply voltage VDD is reduced. Accordingly voltage values of the first reference voltage and the second reference voltage become substantially constant.

The source follower circuit SF1 includes a transistor N3, a level shift element Z1, and a constant current source S1. For example, the transistor N3 is an NMOS transistor. The transistor N3 has a gate terminal, a source terminal, and a drain terminal. The drain terminal of the transistor N3 is connected to a power supply that outputs the power supply voltage VDD. The gate terminal of the transistor N3 is connected to the first terminal of the capacitive element C1.

For example, the level shift element Z1 is a resistor. The level shift element Z1 has a first terminal and a second terminal. The first terminal of the level shift element Z1 is connected to the source terminal of the transistor N3. The constant current source S1 is connected to the second terminal of the level shift element Z1 and the ground. For example, the constant current source S1 is a transistor of which a gate voltage is controlled to be constant.

The first reference voltage is output from the second terminal of the level shift element Z1, and the second reference voltage is output from the first terminal of the level shift element Z1. Accordingly, the reference voltage generation unit 9 generates the first reference voltage and the second reference voltage obtained by shifting a level of the first reference voltage. The amount of level shift can be set according to a resistance value of the level shift element Z1 and a current value of the constant current source S1. The reference voltage generation unit 9 samples and holds a voltage according to the power supply voltage VDD, and generates a first reference voltage and a second reference voltage on the basis of the held voltage.

The configuration of the reference voltage generation unit 9 is not limited to the above configuration. The reference voltage generation unit 9 may generate the first reference voltage and the second reference voltage without sampling and holding the voltage according to the power supply voltage VDD.

Equation (2) shows a current value $I_{DIFF}$ of the differential current.

$$I_{DIFF} = I_{REF} - I_{PIX} \quad (2)$$

In Equation (2), the current value $I_{REF}$ is a value of the reference current generated by the reference current generation unit 8. The current value $I_{PIX}$ is a value of the pixel current generated by the pixel 3. As shown in the Equation (2), the current mirror unit CM1 generates a differential current according to the difference between the pixel current ($I_{PIX}$) and the reference current ($I_{REF}$).

Equation (3) shows a voltage value $V_{OUT}$ of the output signal out the conversion unit I/V1.

$$V_{OUT} = V_{REF1} - R_1 \times I_{DIFF} \quad (3)$$

In Equation (3), the voltage value $V_{REF1}$ is a value of the first reference voltage. The resistance value $R_1$ is a value of the resistor R1. The current value $I_{DIFF}$ is a value of the differential current generated by the current mirror unit CM1. As shown in Equation (3), the conversion unit I/V1 converts the differential current ($I_{DIFF}$) into the output voltage ($V_{OUT}$) whose reference is the first reference voltage ($V_{REF1}$).

For example, the current values of the pixel current at the time of darkness when the amount of incident light is substantially zero and the reference current are the same. In this case, the current value $I_{DIFF}$ of the differential current is substantially zero according to Equation (2). Equation (4) shows a voltage value $V_{OFFSET}$ of the difference between the second reference voltage and the output voltage at the time of darkness.

$$V_{OFFSET} = V_{REF2} - V_{REF1} \quad (4)$$

In Equation (4), the voltage value $V_{REF2}$ is a value of the second reference voltage. The voltage value $V_{REF1}$ is a value of the first reference voltage. As shown in Equation (4), a difference between the second reference voltage and the output voltage at the time of darkness is based only on the first reference voltage and the second reference Voltage. Therefore, the imaging device 1 can accurately secure the value $V_{OFFSET}$ of the difference between the output voltage and the second reference voltage.

The imaging device 1 need not include a capacitive element for noise reduction in a column portion. Therefore, an area of the column portion does not increase. The column portion is a region corresponding to each column in the array of the plurality of pixels 3. For example, the switch unit 5 is arranged in the column portion.

The subsequent-stage circuit 200 obtains a signal component which is a difference between the reset level and the signal level by performing subtraction (CDS process). FIG. 3 shows a configuration of the subsequent-stage circuit 200. As shown in FIG. 3, the subsequent-stage circuit 200 includes an AFE circuit 201, a line memory 202, and a subtractor 203. For example, the AFE circuit 201, the line memory 202, and the subtractor 203 are arranged on a substrate or chip different from the substrate or chip on which the imaging device 1 is arranged.

The output signal Aout from the output unit 7 is input to the AFE circuit 201. That is, the output voltage and the second reference voltage are alternately input to the AFE circuit 201. The AFE circuit 201 converts the output signal Aout into a digital value. That is, the AFE circuit 201 converts a difference signal between the output voltage and the second reference voltage into the digital value. The output voltage is a voltage of the pixel signal at the reset level or the signal level. The line memory 202 holds the digital value of the difference signal between the output voltage at the reset level and the second reference voltage. The subtractor 203 subtracts the digital value of the difference signal between the output voltage at the reset level held in the line memory 202 and the second reference voltage from the digital value of the difference signal between the output voltage at the signal level output from the AFE circuit 201 and the second reference voltage. The subtractor 205 outputs a digital value Asub of the signal component In a case in which the output circuit OUT does not include the selection circuit MUX, the subsequent-stage circuit 200 may include the selection circuit MUX. For example, the output voltage and the second reference voltage are simultaneously input to the selection circuit MUX, and the selection circuit MUX may alternately output the output voltage and the second reference voltage to the AFE circuit 201.

Figure 4:
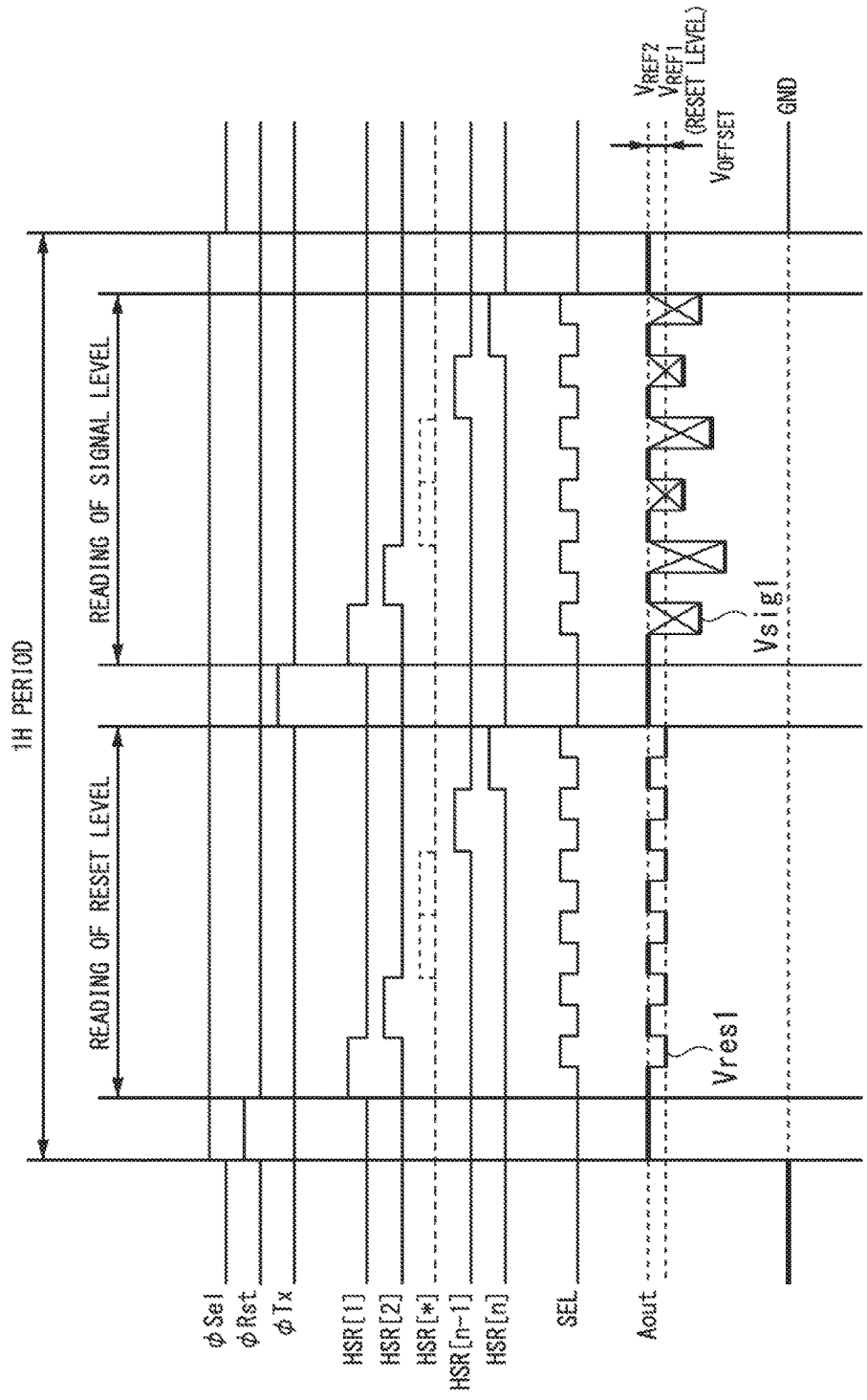
FIG. 4 is a timing chart showing an operation of the imaging device according to the first embodiment of the present invention.

The operation of the imaging device 1 will be described. FIG. 4 shows the operation of the imaging device 1. Hereinafter, an operation of reading the pixel signal in the imaging device 1 will be described.

In FIG. 4, waveforms of the selection pulse φSel, the reset pulse φRst, the transfer pulse φTx, the selection pulse HSR[1] to the selection pulse HSR[n], the selection signal SEL, and the output signal Aout are shown. In FIG. 4, a horizontal direction indicates time and a vertical direction indicates a voltage.

Before the operation of reading the pixel signal is started, the selection pulse φSel, the reset pulse φRst, the transfer pulse φTx, the selection signal SEL, and the selection pulse HSR[1] to the selection pulse HSR[n] are in a low (L) state. Before the operation of reading the pixel signal is started, the output signal Aout is at a ground level (GND).

When the selection pulse φSel output from the vertical selection unit 4 to the pixel 3 in a predetermined row changes from a L state to a high (H) state, the selection transistor Sel is turned on (conductive state). Accordingly, the pixel 3 in the predetermined row is selected.

(Reading of Reset Level)

The reset pulse φRst output from the vertical selection unit 4 to the pixel 3 in the predetermined row changes from the L state to the H state, and accordingly, the reset transistor Rst is turned on. Accordingly, the charge accumulation unit FD is reset and the pixel signal at the reset level is output to the vertical signal line 30. Thereafter, the reset pulse φRst changes from the H state to the L state, and accordingly, the reset transistor Rst is turned off.

Thereafter, the selection pulse HSR[1] output from the horizontal selection unit 6 to the switch transistor SW in the first column changes from the L state to the H state, and accordingly, the switch transistor SW is turned on. Accordingly, the pixel signal at the reset level of the pixel 3 in the first column in a predetermined row is output from the vertical signal line 30 to the horizontal signal line 31. At this time, reading of the reset level is started. The pixel signal at the reset level output to the horizontal signal line 31 is input to the output unit 7. The output unit 7 converts the pixel signal at the reset level input as a current into an output voltage. When the selection signal SEL is in the L state, the output unit 7 outputs the second reference voltage as the output signal Aout to the subsequent-stage circuit 200. When the selection signal SEL changes from the L state to the H state the output unit 7 outputs the output voltage as the output signal Aout to the subsequent-stage circuit 200. Thereafter, the selection pulse HSR[1] changes from the H state to the L state, and accordingly, the switch transistor SW is turned off. Simultaneously, the selection signal SEL changes from the H state to the L state.

In a period in which the selection pulse HSR[1] is in the H state, the AFE circuit 201 of the subsequent-stage circuit 200 converts the differential voltage between the second reference voltage and the output voltage at the reset level into a digital value. The line memory 202 holds the digital value.

Similarly, the selection pulse HSR[2] to the selection pulse HSR[n] sequentially become the H state, and accordingly, the pixel signal at the reset level is transferred from the pixel 3 of each column in the predetermined row to the output unit 7. The output unit 7 converts the sequentially input pixel signals at the reset level into the output voltages and alternately outputs the second reference voltages and the output voltages as the output signals Aout to the subsequent-stage circuit 200. The selection pulse HSR[n] becomes the L state, and accordingly, the reading of the reset level ends.

Since the power supply voltage VDD is input to the gate terminal of the switch transistor SW1, the switch transistor SW1 is turned on. Accordingly, the reference current is transferred from the reference current generation unit 8 to the output unit 7.

In each period in which the selection pulse HSR[2] to the selection pulse HSR[n] are in the H state, the AFE circuit 201 of the subsequent-stage circuit 200 converts the differential voltage between the second reference voltage and the output voltage at the reset level into a digital value. The line memory 202 holds the digital value.

(Reading of Signal Level)

Thereafter, the transfer pulse ɸTx output from the vertical selection unit 4 to the pixel 3 in the predetermined row changes from the L state to the H state, and accordingly, the transfer transistor Tx is turned on. Accordingly, the signal charge of the photoelectric conversion unit PD is transferred to the charge accumulation unit FD, and the pixel signal at the signal level is output to the vertical signal line 30. Thereafter, the transfer pulse ɸTx changes from the H state to the L state, and accordingly, the transfer transistor Tx is turned off.

Thereafter, the selection pulse HSR[1] output from the horizontal selection unit 6 to the switch transistor SW in the first column changes from the L state to the H state, and accordingly, the switch transistor SW is turned on. Accordingly, the pixel signal at the signal level of the pixel 3 of the first column in the predetermined row is output from the vertical signal line 30 to the horizontal signal line 31. In this case, reading of the signal level is started. The pixel signal at the signal level output to the horizontal signal line 31 is input to the output unit 7. The output unit 7 converts the pixel signal at the signal level input as a current into an output voltage. When the selection signal SEL is in the L state, the output unit 7 outputs the second reference voltage as the output signal Aout to the subsequent-stage circuit 200. When the selection signal SEL changes from the L state to the H state, the output unit 7 outputs the output voltage as the output signal Aout to the subsequent stage circuit 200.

Thereafter, the selection pulse HSR[1] changes from the H state to the L state, and accordingly, the switch transistor SW is turned off.

In a period in which the selection pulse HSR[1] is in the H state, the AFE circuit 201 of the subsequent-stage circuit 200 converts the differential voltage between the second reference voltage and the output voltage at the signal level into a digital value. The subtractor 203 subtracts the digital value of the differential voltage between the second reference voltage held in the line memory 202 and the output voltage at the reset level from the digital value of the differential voltage between the second reference voltage and the output voltage at the signal level.

Similarly, the selection pulse HSR[2] to the selection pulse HSR[n] sequentially become the H state, and accordingly, the pixel signal at the signal level is transferred from the pixel 3 of each column in the predetermined row to the output unit 7. The output unit 7 converts the sequentially input pixel signals at the signal level into output voltages and alternately outputs the second reference voltages and the output voltages as output signals Aout to the subsequent-stage circuit 200. The selection pulse HSR[n] becomes the L state, and accordingly, the reading of the signal level ends.

Since the power supply voltage VDD is input to the gate terminal of the switch transistor SW1, the switch transistor SW1 is turned on. Accordingly, the reference current is transferred from the reference current generation unit 8 to the output unit 7.

In each period in which the selection pulse HSR[2] to the selection pulse HSR[n] are in the H state, the AFE circuit 201 of the subsequent-stage circuit 200 converts the differential voltage between the second reference voltage and the output voltage at the signal level into a digital value. The subtractor 203 subtracts the digital value of the differential voltage between the second reference voltage held in the line memory 202 and the output voltage at the reset level from the digital value of the differential voltage between the second reference voltage and the on voltage at the signal level.

By performing the above operation for each row, pixel signals are read from the pixels 3 of all the rows.

The voltage value $V_{REF1}$ of the first reference voltage and the voltage value $V_{REF2}$ of the second reference voltage are shown in FIG. 4. As shown in FIG. 4, the voltage value $V_{OFFSET}$ of the difference between the second reference voltage and the output voltage at the time of darkness is a difference between the voltage value $V_{REF2}$ of the second reference voltage and the voltage value $V_{REF1}$ of the first reference voltage. As shown in FIG. 4, the voltage value of the output voltage Vres1 at the time of resetting of the plurality of pixels 3 is $V_{REF1}$. The output voltage Vres1 at the time of resetting of the plurality of pixels 3 is higher than the output voltage Vsig1 at the time of exposure of the plurality of pixels 3. The second reference voltage ($V_{REF2}$) is set to a voltage higher than the first reference voltage ($V_{REF1}$). Since the second reference voltage is higher than the first reference voltage, it is guaranteed that the second reference voltage is always higher than the output voltage. The difference between the second reference voltage and the output voltage is smallest at the time of darkness. The difference between the second reference voltage and the output voltage at the time of darkness can be secured with high accuracy even at the time of darkness as shown in Equation (4).

Figure 10:
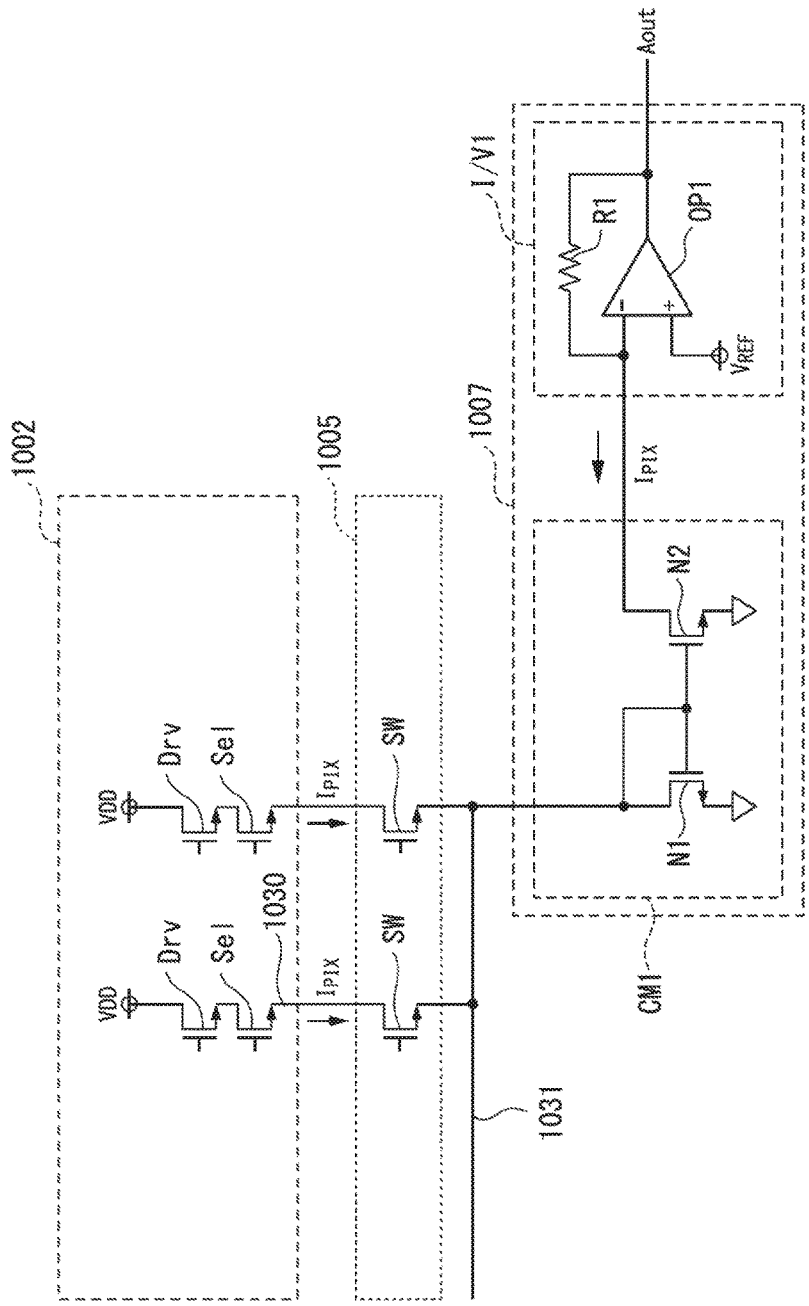
FIG. 10 is a circuit diagram showing a configuration of an output unit in the imaging device of the related art.
Figure 11:
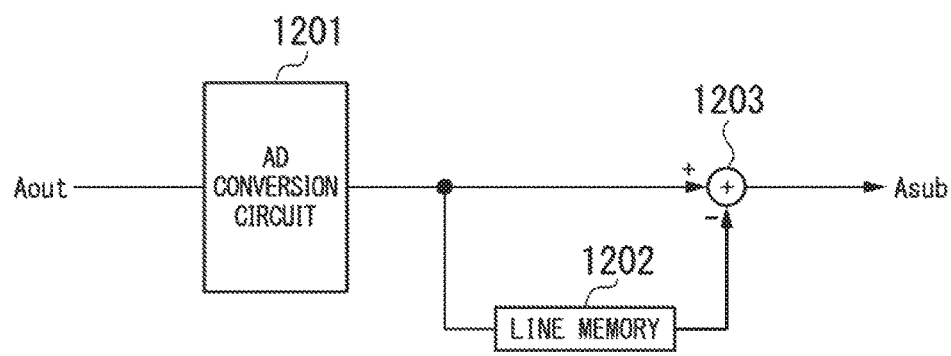
FIG. 11 is a block diagram showing a configuration of a subsequent-stage circuit of the related art.
Figure 12:
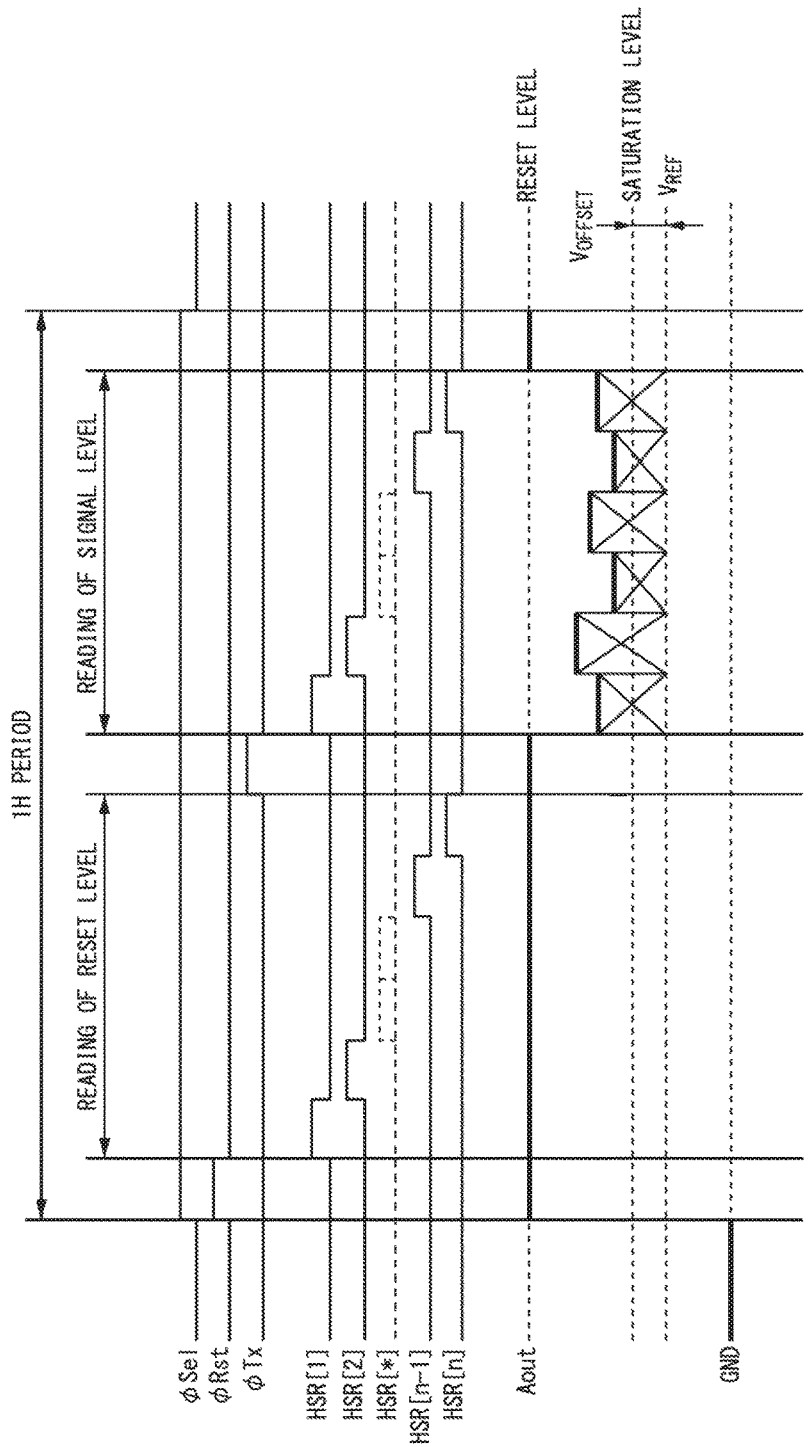
FIG. 12 is a timing chart showing an operation of the imaging device of the related art.

A difference between the output unit 7 shown in FIG. 2 and the output unit 1007 shown in FIG. 10 will be described. In the output unit 1007 shown in FIG. 10, the voltage value $V_{OUT}$ of the output signal Aout is shown in Equation (1). The current value $I_{PIX}$ is smallest at the time of brightness (saturation), but is not zero. Therefore, the voltage value $V_{OUT}$ of the output signal Aout always includes an offset component based on a smallest value of the current value $I_{PIX}$. As a result, a range in which the characteristics of the input voltage and the output voltage of the operational amplifier OP1 included in the output unit 1007 are linear is limited by the offset component. On the other hand, in the output unit 7 shown in FIG. 2, the voltage value $V_{OUT}$ of the output signal Aout is shown in Equation (3). Since the current value $I_{DIFF}$ of the differential current at the time of darkness is substantially zero, the voltage value $V_{OUT}$ of the output signal Aout does not include the above offset component. As a result, the imaging device 1 can effectively use the range in which the characteristics of the input voltage and the output voltage of the operational amplifier OP1 included in the output unit 7 are linear.

The transistor included in the pixel 3 and the switch transistor SW included in the switch unit 5 may be PMOS transistors. When a conductivity type of the transistor is changed, a direction of the differential current changes. A voltage when a PMOS transistor is used for the pixel 3 and the switch unit 5 will he described.

Equation (5) shows the voltage value $V_{OUT}$ of the of signal Aout of the conversion unit I/V1.

$$V_{OUT} = V_{REF1} + R1 \times I_{DIFF} \quad (5)$$

In Equation (5), the voltage value $V_{REF1}$ is a value of the first reference voltage. The resistance value $R_1$ is a value of the resistor R1. The current value $I_{DIFF}$ is a value of the differential current generated by the current mirror unit CM1.

For example, the current values of the pixel current at the time of darkness when the amount of incident light is substantially zero and the reference current are the same. In this case, the current value $I_{DEFF}$ of the differential current is substantially zero according to Equation (5). Equation (6) shows a voltage value $V_{OFFSET}$ of the difference between the second reference voltage and the output voltage at the time of darkness.

$$V_{OFFSET} = V_{REF1} - V_{REF2} \quad (6)$$

In Equation (6), the voltage value $V_{REF1}$ is a value of the first reference voltage. The voltage value $V_{REF2}$ is a value of the second reference voltage. As shown in Equation (6), a difference between the second reference voltage and the output voltage at the time of darkness is based only on the first reference voltage and the second reference voltage. Therefore, the imaging device 1 can accurately secure the value $V_{OFFSET}$ of the difference between the output voltage and the second reference voltage.

Figure 5:
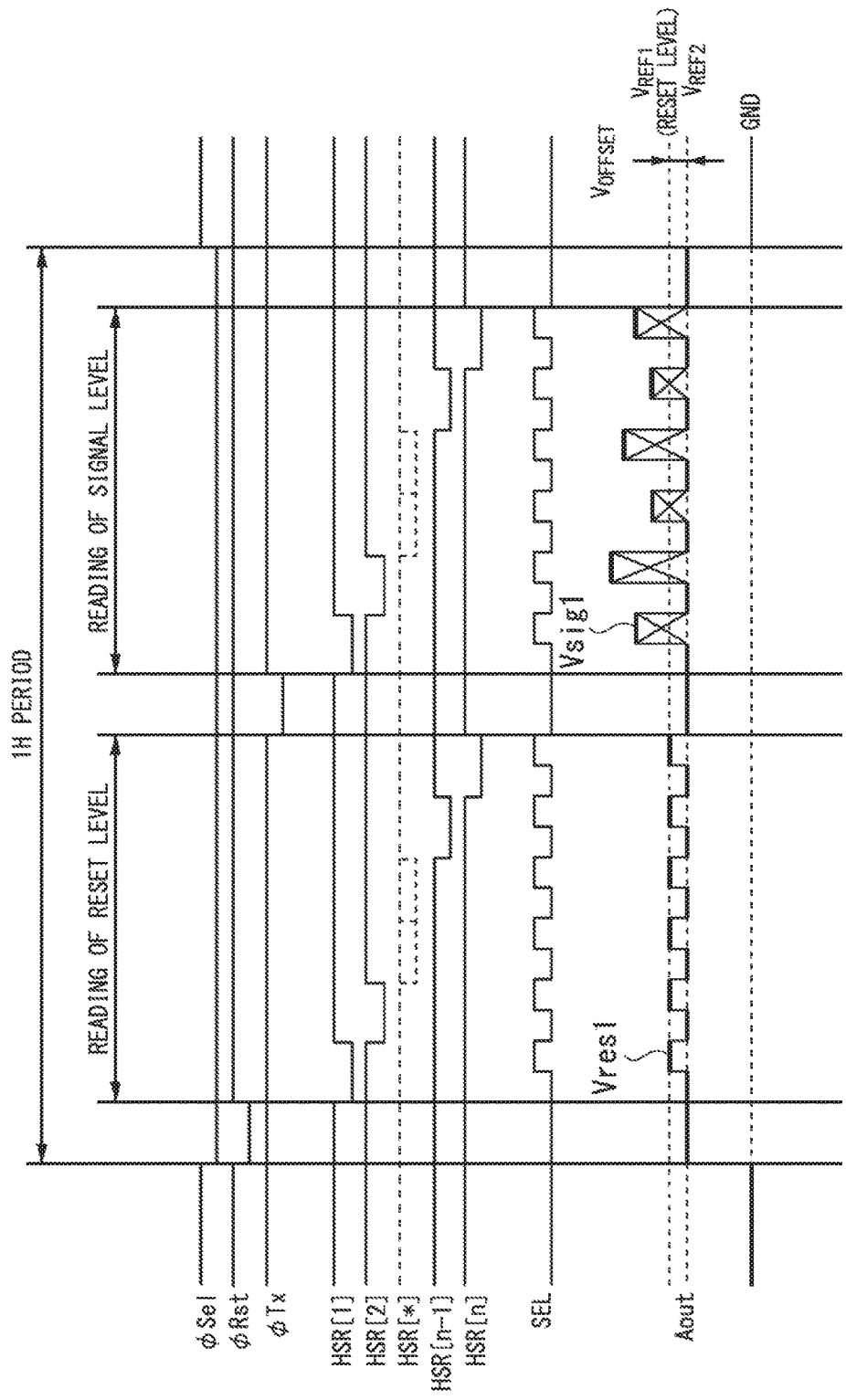
FIG. 5 is a timing chart showing an operation of the imaging device according to the first embodiment of the present invention.

FIG. 5 shows an operation of the imaging device 1. In FIG. 5, the waveforms of the selection pulse φSel, the reset pulse φRst, the transfer pulse φTx, the selection pulse HSR[1] to the selection pulse HSR[n], the selection signal SEL, and the output signal Aout are shown. In FIG. 5, a horizontal direction indicates time and a vertical direction indicates the voltage.

Difference between FIG. 5 and FIG. 4 will be described. In FIG. 5, the state of each pulse is opposite to the state a each pulse shown in FIG. 4. When the selection pulse φSel is in the H state, the selection transistor Sel is off and when the selection pulse φSel is in the L state, the selection transistor Sel is on. When the reset pulse φRst is in the H state, the reset transistor Rst is off and when the reset pulse φRst is in the L state, the reset transistor Rst is on. When the selection pulse HSR[i] is in the H state, the switch transistor SW is off and when the selection pulse HSR [i] is in the L state, the switch transistor SW is on. i is an integer from 1 to n.

In FIG. 5, the operation of reading the pixel signal in the imaging device 1 is the same as the operation shown in FIG. 4. The voltage value $V_{REF1}$ of the first reference voltage and the voltage value $V_{REF2}$ of the second reference voltage are shown in FIG. 5. As shown in Equation (6), the voltage value $V_{OFFSET}$ of the difference between the second reference voltage and the output voltage at the time of darkness is a difference between the voltage value $V_{REF1}$ of the first reference voltage and the voltage value $V_{REF2}$ of the second reference voltage. As shown in FIG. 5, the voltage value of the output voltage Vres1 at the time of resetting of the plurality of pixels 3 is $V_{REF1}$. The output voltage Vres1 at the time of resetting of the plurality of pixels 3 is lower than the output voltage Vsig1 at the time of exposure of the plurality of pixels 3. The second reference voltage ($V_{REF2}$) is set to a voltage lower than the first reference voltage ($V_{REF1}$). Since the second reference voltage is lower than the first reference voltage, it is guaranteed that the second reference voltage is always lower than the output voltage. The difference between the second reference voltage and the output voltage is smallest at the time of darkness. The difference between the second reference voltage and the output voltage at the time of darkness can be secured with high accuracy even at the time of darkness as shown in Equation (6).

The imaging device according to each aspect of the present invention need not have a configuration corresponding to at least one of the vertical selection unit 4, the switch unit 5, and the horizontal selection unit 6. The imaging device of each aspect of the present invention need not have a configuration corresponding to the selection transistor Sel among elements of the pixel 3. The imaging device according to each aspect of the present invention need not have a configuration corresponding to the selection transistor Sel1 among the elements of the reference current generation unit 8.

As described above, the imaging device 1 includes the plurality of pixels 3, the reference current generation unit 8 (reference current generation circuit), the current mirror unit CM1 (differential current generation circuit), the reference voltage generation unit 9 (reference voltage generation circuit), the conversion unit I/V1 (conversion circuit), and the output circuit OUT. The plurality of pixels 3 output a pixel current according to the incident light. The reference current generation unit 8 generates the reference current. The pixel current and the reference current are input to the current mirror unit CM1. The current mirror unit CM1 generates the differential current according to the difference between the pixel current and the reference current. The reference voltage generation unit 9 generates the first reference voltage and the second reference voltage. The differential current and the first reference voltage are input to the conversion unit I/V1. The conversion unit I/V1 converts the differential current into the output voltage on the basis of the first reference voltage. The output voltage and the second reference voltage are input to the output circuit OUT. The output circuit OUT outputs the output voltage and the second reference voltage. When the output voltage at the time of resetting of the plurality of pixels 3 is higher than the output voltage at the time of exposure of the plurality of pixels 3, the second reference voltage is higher than the first reference voltage. When the output voltage at the time of resetting of the plurality of pixels 3 is lower than the output voltage at the time of exposure of the plurality of pixels 3, the second reference voltage is lower than the first reference voltage.

In the first embodiment, since the first reference voltage and the second reference voltage satisfy the above relationship, the accuracy of the voltage difference is improved. Therefore, the subsequent-stage circuit 200 can perform signal processing with high accuracy.

In the first embodiment, the output circuit OUT alternately outputs the output voltage and the second reference voltage. The subtractor 203 performs subtraction on a combination of the output voltage continuously output from the output unit 7 with the second reference voltage. When long-cycle noise is superimposed on a signal, the amounts of long-cycle noise superimposed on the output voltage that is output continuously and the second reference voltage are substantially the same. Therefore, even when the long-cycle noise is superimposed on the reference voltage, the noise component is suppressed by the subtraction.

In the first embodiment, the reference current generation unit 8 includes the transistor Nref1 of which the gate terminal and the drain terminal are electrically connected to each other. Therefore, the reference current generation unit 8 can generate the reference current with a simple configuration.

Second Embodiment

Figure 6:
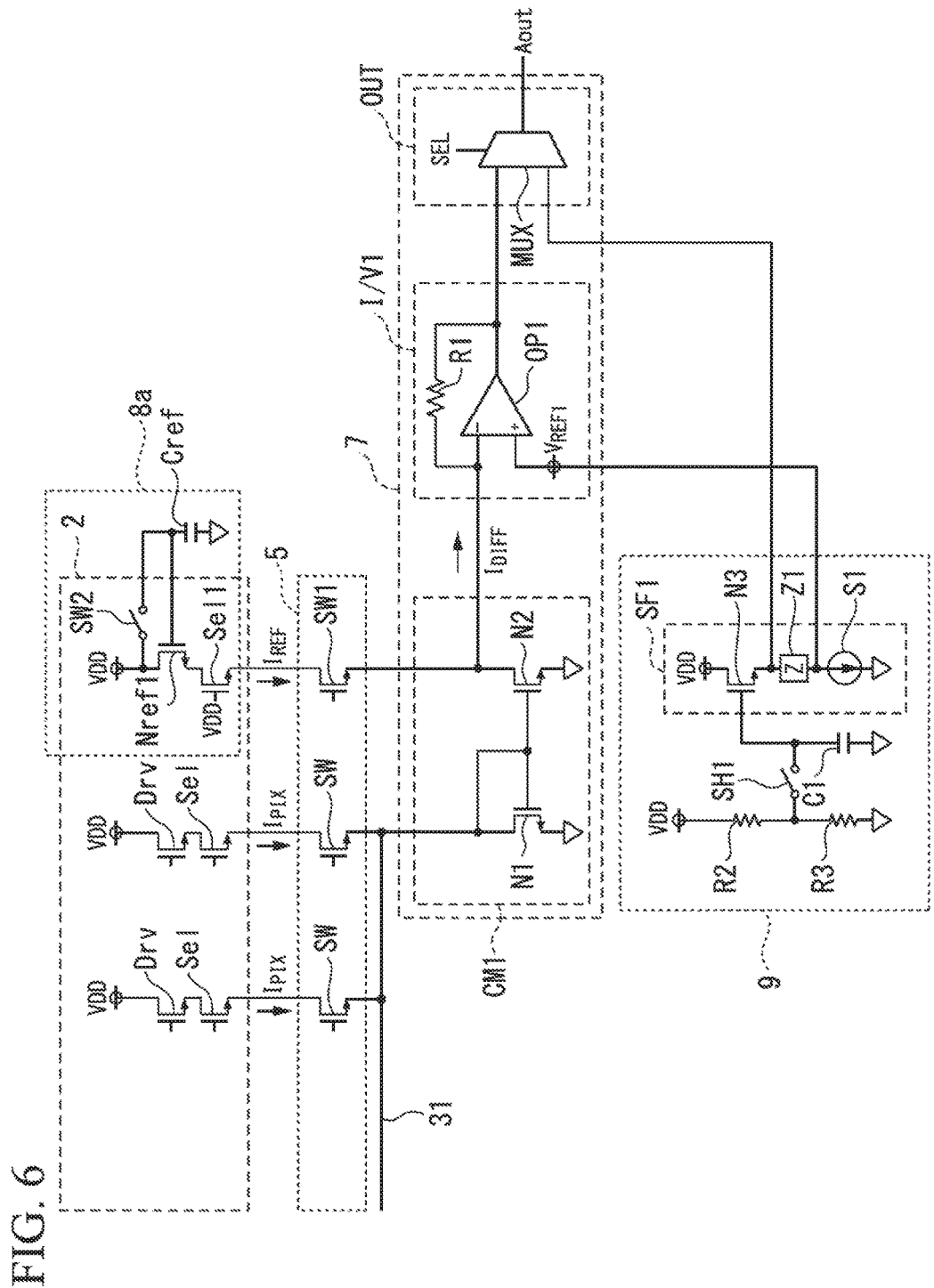
FIG. 6 is a circuit diagram showing a configuration of an output unit, a reference current generation unit, and a reference voltage generation unit in an imaging device according to a second embodiment of the present invention.

In a second embodiment of the present invention, the reference current generation unit 8 in the first embodiment is changed to a reference current generation unit 8a shown in FIG. 6.

FIG. 6 shows a configuration of an output unit 7, the reference current generation unit 8a, and a reference voltage generation unit 9. Differences between the configuration shown in FIG. 6 and the configuration shown in FIG. 2 will be described. As shown in FIG. 6, the reference current generation unit 8a includes a transistor Nref1, a selection transistor Sel1, a switch SW2, and a capacitive element Cref. For example, the transistor Nref1 and the selection transistor Sel1 are NMOS transistors. The transistor Nref1 and the selection transistor Sel1 have a gate terminal, a source terminal, and a drain terminal. The switch SW2 may be a transistor.

The chain terminal of the transistor Nref1 is connected to a power supply that outputs a power supply voltage VDD. The source terminal of the transistor Nref1 is connected to the selection transistor Sel1. The transistor Nref1 outputs a reference current from the source terminal. For example, a current value of the reference current is the same as a current value of a pixel signal at the time of darkness when the amount of incident light is substantially zero.

The drain terminal of the selection transistor Sel1 is connected to the source terminal of the transistor Nref1. The source terminal of the selection transistor Sel1 is connected to the switch unit 5. The gate terminal of the selection transistor Sel1 is connected to the power supply that outputs the power supply voltage VDD. A reference current flows between the drain terminal of the selection transistor Sel1 and the source terminal of the selection transistor Sel1. The selection transistor Sel1 outputs, from the source terminal, the reference cumin output from the transistor Nref1.

The switch SW2 has a first terminal and a second terminal. The first terminal of the switch SW2 is connected to the gate terminal of the transistor Nref1. The second terminal of the switch SW2 is connected to the power supply that outputs the power supply voltage VDD.

The capacitive element Cref has a first terminal and a second terminal. The first terminal of the capacitive element Cref is connected to the gate terminal of the transistor Nref1 and the first terminal of the switch SW2. The second terminal of the capacitive element Cref is connected to a ground.

The switch SW2 is an element capable of switching between ON and OFF. When the switch SW2 is ON, the first terminal of the capacitive element Cref is electrically connected to the power supply. When the switch SW2 is OFF, the first terminal of the capacitive element Cref is electrically insulated from the power supply.

The switch SW2 and the capacitive element Cref constitute a sample and hold circuit. The switch SW2 samples the power supply voltage VDD. The capacitive element Cref holds the voltage sampled by the switch SW2. That is, the capacitive element Cref is a sampling capacitor. By sampling the power supply voltage VDD, an influence of noise superimposed on the power supply voltage VDD is reduced. As a result, the current value $I_{REF}$ of the reference current becomes substantially constant.

A configuration of the reference current generation unit 8a is not limited to the, above configuration. A part of the reference current generation unit 8a may be configured similarly to the pixel 3. For example, the transistor Nref1 way be configured similarly to the amplification transistor Drv. For example, the selection transistor Sel1 may be configured similarly to the selection transistor Sel. In FIG. 6, the transistor Nref1, the selection transistor Sel1, and the switch SW2 are part of the imaging unit 2. However, the transistor Nref1, the selection transistor Sel1, and the switch SW2 may be configured independently of the imaging unit 2. The transistor Nref1 and the selection transistor Sel1 may be PMOS transistors.

Apart from the above differences, the configuration shown in FIG. 6 is the same as the configuration shown in FIG. 2.

As described above, each of the plurality of pixels 3 includes the photoelectric conversion unit PD, the transfer transistor Tx (charge transfer unit), the charge accumulation unit FD, and the signal generation unit. The photoelectric conversion unit PD generates signal charge according to the incident light. The transfer transistor Tx transfers the signal charge generated by the photoelectric conversion unit PD. The charge accumulation unit FD accumulates the signal charge transferred by the transfer transistor Tx. The signal generation unit generates a pixel current according to the voltage of the charge accumulation unit FD. The signal generation unit is the amplification transistor Drv (first MOS transistor). The amplification transistor Drv has a drain terminal (a first drain terminal) and a source terminal (a first source terminal). A pixel current flows between the drain terminal of the amplification transistor Drv and the source terminal of the amplification transistor Drv.

As described above, the reference current generation unit Sa includes the transistor Nref1 (second MOS transistor), the switch SW2, and the capacitive element Cref. The transistor Nref1 has the gate terminal, the drain terminal (a second drain terminal), and the source terminal (a second source terminal). A reference current flows between the drain terminal of the transistor Nref1 and the source terminal of the transistor Nref1. The switch SW2 has the first terminal connected to the gate terminal of the transistor Nref1 and the second terminal connected to the drain terminal of the transistor Nref1. The capacitive element Cref is connected to the gate terminal of the transistor Nref1.

The imaging device of each aspect of the present invention need not have a configuration corresponding to the selection transistor Sel1 among the elements of the reference current generation unit 8a.

In the second embodiment, the accuracy, of the voltage difference is improved due to the relationship between the first reference voltage and the second reference voltage. Therefore, the subsequent-stage circuit 200 can perform signal processing with high accuracy.

In the second embodiment, the reference current generation unit 8a includes the switch SW2 and the capacitive element Cref. Therefore, the reference current generation unit 8a can generate the reference current with high resistance to fluctuations of the power supply voltage VDD. As a result, a power supply voltage variation rejection ratio (PSRR) of the reference current generation unit 8a is improved.

Third Embodiment

Figure 7:
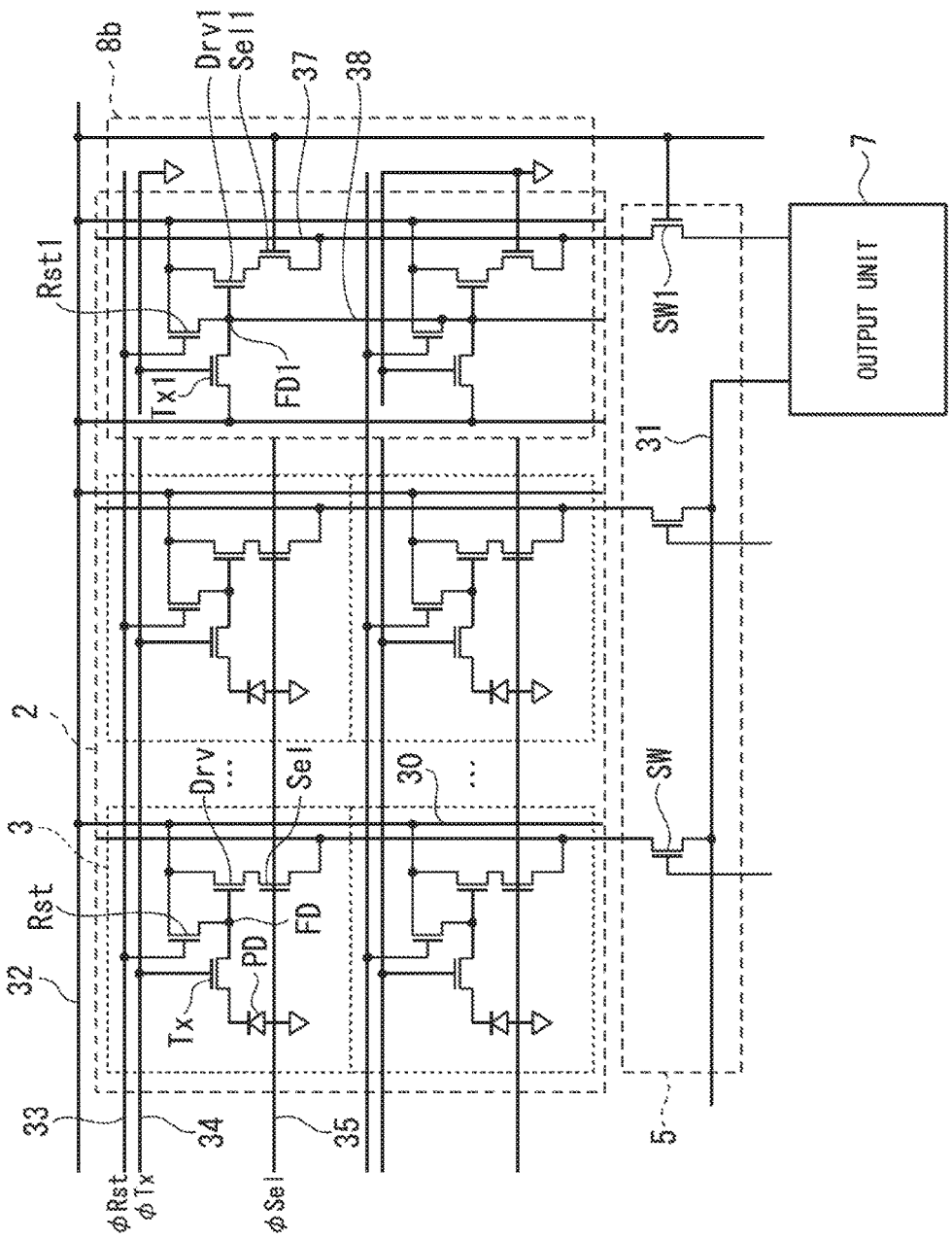
FIG. 7 is a circuit diagram showing a configuration of an imaging unit, a switch unit, and a reference current generation unit in an imaging device according to a third embodiment of the present invention.

In a third embodiment of the present invention, the reference current generation unit 8 in the first embodiment is changed to a reference current generation unit 8b shown in FIG. 7.

FIG. 7 Shows a configuration of an imaging unit 2, a switch unit 5, and a reference current generation unit 8b. Differences between the reference current generation unit 8b and the reference current generation unit 8 shown in FIG. 2 will be described. In FIG. 7, two rows of pixels 3 among a plurality of pixels 3 included in the imaging unit 2 are shown, and pixels 3 of the other rows are omitted. As shown in FIG. 7, the reference current generation unit 8b includes a plurality of transfer transistors Tx1, a plurality of charge accumulation units FD1, a plurality of reset transistors Rst1, a plurality of amplification transistors Drv1, and a plurality of selection transistors Sel1. In FIG. 7, the reference current generation unit 8b includes two transfer transistors Tx1, two charge accumulation units FD1, two reset transistors Rst1, two amplification transistors Drv1, and two selection transistors Sel1. For example, each of the transfer transistor Tx1, the reset transistor Rst1, the amplification transistor Drv1, and the selection transistor Sel1 is an NMOS transistor. Each of the transfer transistor Tx1, the reset transistor Rst1, the amplification transistor Drv1, and the selection transistor Sel1 has a gate terminal, a source terminal, and a drain terminal.

The drain terminal of the transfer transistor Tx1 is connected to a power supply line 32. The source terminal of the transfer transistor Tx1 is connected to the charge accumulation unit FD1. The gate terminal of the transfer transistor Tx1 is connected to a ground.

The drain terminal of the reset transistor Rst1 is connected to the power supply line 32. The source terminal of the reset transistor Rst1 is connected to the charge accumulation unit FD1. The gate terminal of the reset transistor Rst1 is connected to a control signal line 33.

The drain terminal of the amplification transistor Drv1 is connected to the power supply line 32. The source terminal of the amplification transistor Drv1 is connected to the selection transistor Sel1. The gate terminal of the amplification transistor Drv1 is connected to the charge accumulation unit FD1. The amplification transistor Drv1 outputs the reference current from the source terminal. For example, a current value of the reference current is the same as a current value of a pixel signal at the time of darkness when the amount of incident light is substantially zero.

Each of the plurality of charge accumulation units FD1 is connected to a signal line 38. The signal line 38 is connected to the gate terminal of each of the plurality of amplification transistors Drv1. Accordingly, the gate terminals of the plurality of amplification transistors Drv1 are connected to each other. In FIG. 7, the gate terminals of the two amplification transistors Drv1 are connected to each other. According to the above configuration, the plurality of charge accumulation units FD1 are electrically connected to each other. That is, a plurality of charge accumulation units FD1 constitute a capacitive element.

The drain terminal of the selection transistor Sel1 is connected to the source terminal of the amplification transistor Drv1. The source terminal of the selection transistor Sel1 is connected to a vertical signal line 37. The gate terminal of one of the plurality of selection transistors Sel1 is connected to the power supply line 32. The gate terminals of the remaining selection transistors Sel1 are connected to the ground. The vertical signal line 37 is connected to the switch transistor SW1. A reference current flows between the drain terminal of the selection transistor Sel1 of which the gate terminal is connected to the power supply line 32 and the source terminal of the selection transistor Sel1. The selection transistor Sel1 of which the gate terminal is connected to the power supply line 32 outputs, from the source terminal, the reference current output from the amplification transistor Drv1.

The transfer transistor Tx1 is turned off due to a ground voltage applied to the gate terminal. The reset transistor Rst1 is controlled by a reset pulse φRst output from a vertical selection unit 4. One of the plurality of selection transistors Sel1 is turned on due to the power supply voltage VDD applied to the gate terminal. The remaining selection transistors Sel1 are turned off due to the ground voltage applied to the gate terminal.

When the charge accumulation unit FD in the pixel 3 is reset, the charge accumulation unit FD1 is reset. In this case, a signal based on the voltage of the charge accumulation unit FD1 is output to the vertical signal line 37. That is, the reference current is output to the vertical signal line 37. When a capacity of the charge accumulation unit FD1 is large, an influence of noise superimposed on the voltage of the charge accumulation unit FD1 is reduced. Since the two charge accumulation units FD1 constitute the capacitive element, the influence of noise superimposed on the voltage of the charge accumulation unit FD1 is reduced.

The reference current generation unit 8b does not include a photoelectric conversion element. Therefore, an area of the reference current generation unit 8b is reduced.

The configuration of the reference current generation unit 8b is not limited to the above configuration. In FIG. 7, the transfer transistor Tx1, the charge accumulation unit FD1, the reset transistor Rst1, the amplification transistor Drv1, and the selection transistor Sel1 are part of the imaging unit 2. However, the transfer transistor Tx1, the charge accumulation unit FD1, the reset transistor Rst1, the amplification transistor Drv1, and the selection transistor Sel1 may be configured independently of the imaging unit 2. The transfer transistor Tx1, the reset transistor Rst1, the amplification transistor Drv1, and the selection transistor Sel1 may be PMOS transistors. Three or more charge accumulation units FD1 may be connected to the respective gate terminals of three or more amplification transistors Drv1, and the respective gate terminals of three or more amplification transistors Drv1 may be connected to each other.

As described above, each of the plurality of pixels 3 includes the photoelectric conversion unit PD, the transfer transistor Tx (charge transfer unit), the charge accumulation unit FD (first charge accumulation unit), and the signal generation unit. The photoelectric conversion unit PD generates first signal charge according to incident light. The transfer transistor Tx transfers the first signal charge generated by the photoelectric conversion unit PD. The charge accumulation unit FD accumulates the first charge transferred by the transfer transistor Tx. The signal generation unit generates a pixel current according to the voltage of the charge accumulation unit FD. The signal generation unit is an amplification transistor Drv (first MOS transistor). The amplification transistor Drv has a drain terminal (a first drain terminal) and a source terminal (a first source terminal). A pixel current flows between the drain terminal of the amplification transistor Drv and the source terminal of the amplification transistor Drv.

As described above, the reference current generation unit 8b (reference current generation circuit) includes a plurality of charge accumulation units FD1 (second charge accumulation units) that accumulate second signal charge and a plurality of amplification transistors Drv1 (second MOS transistors). Each of the plurality of amplification transistors Drv1 has a gate terminal, a drain terminal (a second drain terminal), and a source terminal (a second source terminal). A reference current flows between the drain terminal of the amplification transistor Drv1 and the source terminal of the amplification transistor Drv1. The plurality of charge accumulation units FD1 are connected to the respective gate terminals of the plurality of amplification transistors Drv1. The gate terminals of the plurality of amplification transistors Drv1 are connected to each other.

The imaging device according to each aspect of the present invention need not have a configuration corresponding to at least one of the transfer transistor Tx1, the reset transistor Rst1 and the selection transistor Sel1 among the elements of the reference current generation unit 8b.

In the third embodiment, the accuracy of the voltage difference is improved due to the relationship between the first reference voltage and the second reference voltage. Therefore, the subsequent-stage circuit 200 can perform signal processing with high accuracy.

In the third embodiment, since the capacitive element is constituted by the plurality of charge accumulation units FD1, an influence of noise superimposed on the voltages of the plurality of charge accumulation units FD1 is reduced. That is, the influence of noise on the reference current is reduced.

Fourth Embodiment

Figure 8:
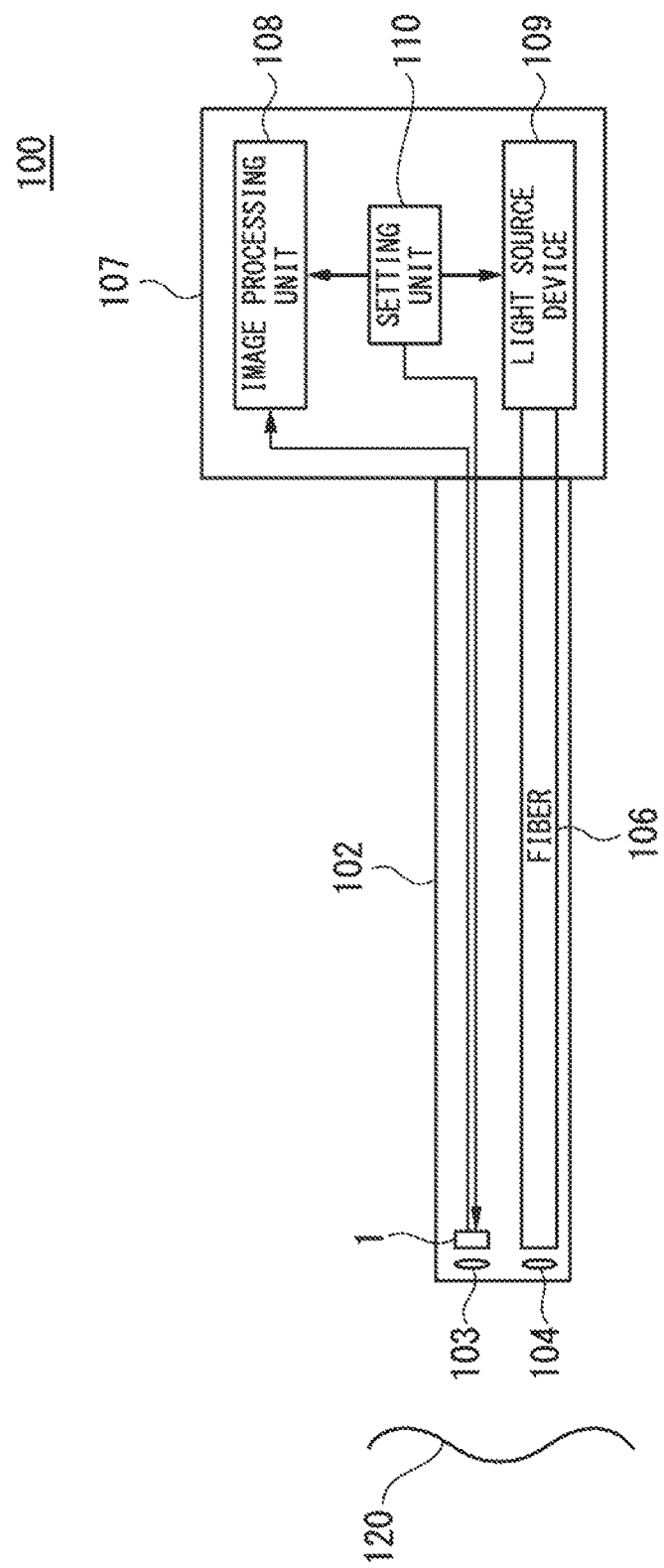
FIG. 8 is a block diagram showing a configuration of an endoscope system according to a fourth embodiment of the present invention.
Figure 9:
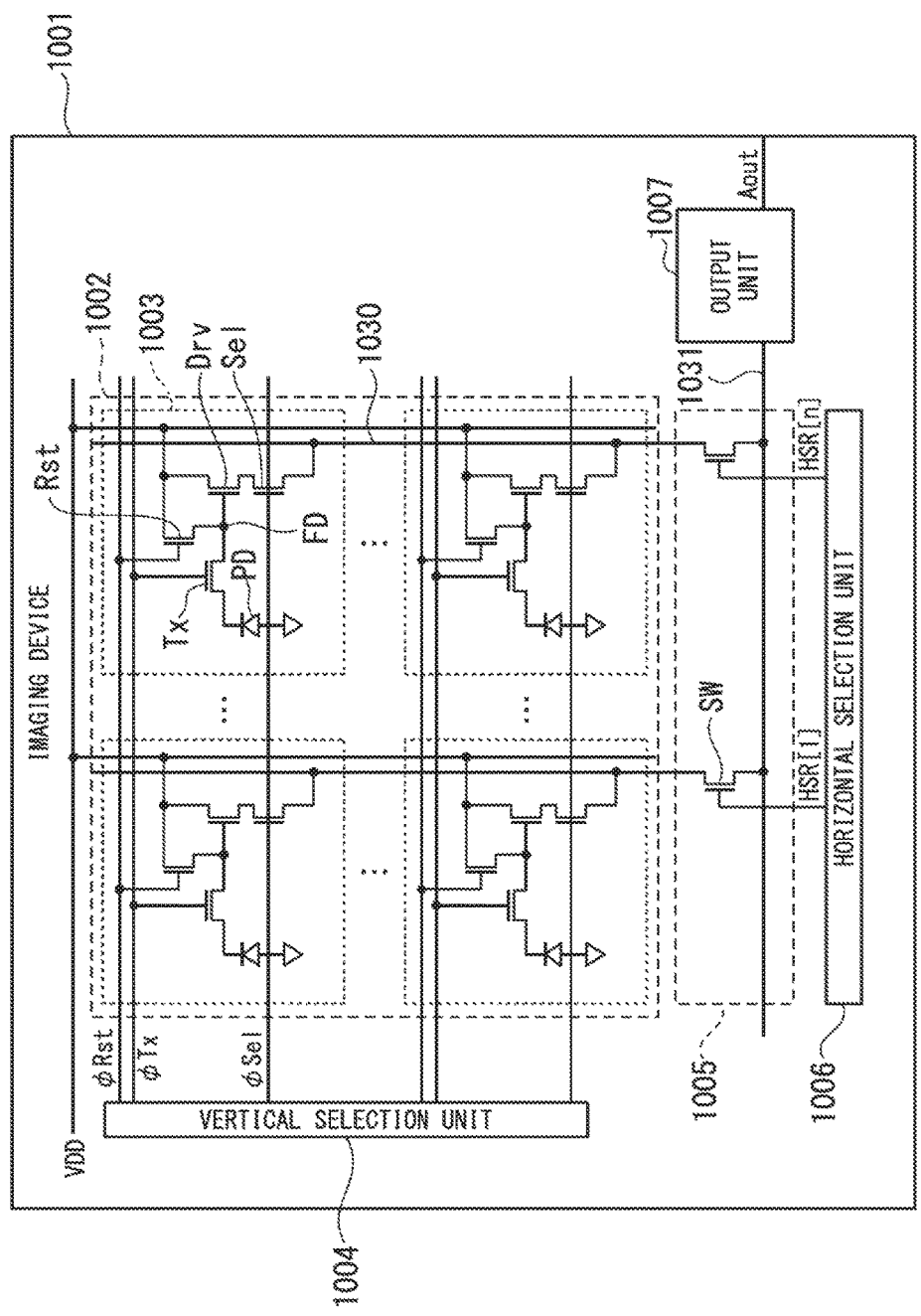
FIG. 9 is a block diagram showing a configuration of an imaging device of the related art.

FIG. 8 shows a configuration of an endoscope system 100 according to a fourth embodiment of the present invention. The endoscope system 100 includes the imaging device 1 according to any one of the first to third embodiments. As shown in FIG. 8, the endoscope system 100 includes a scope 102 and a housing 107. The scope 102 includes the imaging device 1, a lens 103, a lens 104, and a fiber 106. The housing 107 includes an image processing unit 108, a light source device 109, and a setting unit 110.

The imaging device 1 is the imaging device 1 of any one of the first to third embodiments. The lens 103 forms an image of reflected light from the subject 120 on the imaging device 1. The fiber 106 transfers illumination light with which the subject 120 is irradiated. The lens 104 irradiates the subject 120 with the illumination light transferred by the fiber 106. The light source device 109 includes a light source that generates the illumination light with which the subject 120 is irradiated. The image processing unit 108 generates a captured image by performing a predetermined process on the signal output from the imaging device 1. The image processing unit 108 includes a circuit corresponding to the subsequent-stage circuit 200. The setting unit 110 controls an imaging mode of the endoscope system 100.

The configuration of the endoscope system 100 is not limited to the above configuration. The endoscope system of each aspect of the present invention need not have a configuration corresponding to at least one of the lens 103, the lens 104, the fiber 106, the image processing unit 108, the light source device 109, and the setting unit 11.

In the fourth embodiment, the accuracy of the voltage difference is improved by applying the imaging device 1 of any one of the first to third embodiments. Therefore, the image processing unit 108 can perform signal processing with high accuracy.

Since an increase in an area of the column portion in the imaging device 1 is avoided, it is possible to constitute the thin scope 102.

While preferred embodiments of the invention have been described and shown above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An imaging device, comprising:
   a plurality of pixels configured to output a pixel current according to incident light;
   a reference current generation circuit configured to generate a reference current;
   a differential current generation circuit to which the pixel current and the reference current are input, and configured to generate a differential current according to a difference between the pixel current and the reference current;
   a reference voltage generation circuit configured to generate a first reference voltage and a second reference voltage;
   a conversion circuit to which the differential current and the first reference voltage are input, and configured to convert the differential current into an output voltage on the basis of the first reference voltage; and
   an output circuit to which the output voltage and the second reference voltage are input, and configured to output the output voltage and the second reference voltage,
   wherein the second reference voltage is higher than the first reference voltage when the output voltage at the time of resetting of the plurality of pixels is higher than the output voltage at the time of exposure of the plurality of pixels, and
   the second reference voltage is lower than the first reference voltage when the output voltage at the time of resetting of the plurality of pixels is lower than the output voltage at the time of exposure of the plurality of pixels.

2. The imaging device according to claim 1,
   wherein the output circuit alternately outputs the output voltage and the second reference voltage.

3. The imaging device according to claim 1,
   wherein each of the plurality of includes a photoelectric conversion unit configured to: generate signal charge according to the incident light, a charge transfer unit configured to transfer the Signal charge generated by the photoelectric conversion unit, a charge accumulation unit configured to accumulate the signal charge transferred by the charge transfer unit; and a signal generation unit configured to generate the pixel current according to the voltage of the charge accumulation unit, the signal generation unit is a first MOS transistor, the first MOS transistor has a first drain terminal and a first source terminal, the pixel current flowing between the first drain terminal and the first source terminal, the reference current generation circuit includes a second MOS transistor, the second MOS transistor has a gate terminal, a second drain terminal, and a second source terminal, the reference current flowing between the second drain terminal and the second source terminal, and the gate terminal and the second drain terminal are electrically connected to each other.

4. The imaging device according to claim 1, wherein each of the plurality of pixels includes a photoelectric conversion unit configured to generate signal charge according to the incident light, a charge transfer unit configured to transfer the signal charge generated by the photoelectric conversion unit, a charge accumulation unit configured to accumulate the signal charge transferred by the charge transfer unit, and a signal generation unit configured to generate the pixel current according to the voltage of the charge accumulation unit, the signal generation unit is a first MOS transistor, the first MOS transistor has a first drain terminal and a first source terminal, the pixel current flowing between the first drain terminal and the first source terminal, the reference current generation circuit includes a second MOS transistor, a switch, and a capacitive element, the second MOS transistor has a gate terminal, a second drain terminal, and a second source terminal, the reference current flowing between the second drain terminal and the second source terminal, the switch has a first terminal connected to the gate terminal and a second terminal connected to the second drain terminal, and the capacitive element is connected to the gate terminal.

5. The imaging device according to claim 1, wherein each of the plurality of pixels includes a photoelectric conversion unit configured to generate first signal charge according to the incident light, a charge transfer unit configured to transfer the first signal charge generated by the photoelectric conversion unit, a first charge accumulation unit configured to accumulate the first signal charge transferred b the charge transfer unit, and a signal generation unit configured to generate the pixel current according to the voltage of the first charge accumulation unit, the signal generation unit is a first MOS transistor, the first MOS transistor has a first drain terminal and a first source terminal, the pixel current flowing between the first drain terminal and the first source terminal, the reference current generation circuit includes:

a plurality of second charge accumulation units configured to accumulate second signal charge, and a plurality of second MOS transistors, each of the plurality of second MOS transistors has a gate terminal, a second drain terminal, and a second source terminal, the reference current flowing between the second drain terminal and the second source terminal, each of the plurality of second charge accumulation units is connected to the gate terminal of each of the plurality of second MOS transistors, and the gate terminals of the plurality of second MOS transistors are connected to each other.

6. An endoscope system having the imaging device according to claim 1.

* * * * *